US008586890B2

(12) United States Patent
Takahashi et al.

(10) Patent No.: US 8,586,890 B2
(45) Date of Patent: Nov. 19, 2013

(54) METHODS OF SEPARATING, IDENTIFYING AND DISPENSING SPECIMEN AND DEVICE THEREFOR, AND ANALYZING DEVICE METHOD

(75) Inventors: Toru Takahashi, Tokyo (JP); Ken Tsukii, Tokyo (JP); Jie Xu, Tokyo (JP)

(73) Assignee: The Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 13/561,941

(22) Filed: Jul. 30, 2012

(65) Prior Publication Data

US 2013/0026180 A1 Jan. 31, 2013

Related U.S. Application Data

(63) Continuation of application No. 11/587,210, filed as application No. PCT/JP2005/007848 on Apr. 25, 2005, now Pat. No. 8,264,674.

(30) Foreign Application Priority Data

Apr. 23, 2004 (JP) ................................ 2004-128467
Sep. 27, 2004 (JP) ................................ 2004-280187

(51) Int. Cl.
*B07C 5/00* (2006.01)
(52) U.S. Cl.
USPC .............. 209/577; 209/599; 222/420; 436/63
(58) Field of Classification Search
USPC ........ 356/335–343, 73; 436/63, 164, 172, 50; 209/3.1, 552, 577, 639, 644, 906, 130, 209/579, 596, 599; 435/2; 222/420
See application file for complete search history.

(56) References Cited

U.S. PATENT DOCUMENTS

| 4,781,460 A | 11/1988 | Bott |
| 5,180,065 A * | 1/1993 | Touge et al. .................. 209/577 |
| 5,275,787 A * | 1/1994 | Yuguchi et al. ............ 422/82.08 |
| 5,674,743 A | 10/1997 | Ulmer |

(Continued)

FOREIGN PATENT DOCUMENTS

| JP | 4-310863 | 11/1992 |
| JP | 7-294412 | 11/1995 |

(Continued)

OTHER PUBLICATIONS

T. Yamashita, et al. "Cell Technology", vol. 16, No. 10, 1997, pp. 1532-1541.

(Continued)

*Primary Examiner* — Hoa Pham
(74) *Attorney, Agent, or Firm* — Oblon, Spivak, McClelland, Maier & Neustadt, L.L.P.

(57) ABSTRACT

A specimen sorter includes a separating device to remove a specimen from a container, a detection device to identify the specimen as a target specimen or a non-target specimen, and a dispensing device to dispense the specimen. The dispensing device includes a dispensing nozzle to contact a vibration member to form liquid droplets at a front end of the dispensing nozzle and to dispense the liquid droplets, a first container to collect the liquid droplets dispensed from the dispensing nozzle that contain the target specimen, and a second container to collect the liquid droplets dispensed from the dispensing nozzle that contain the non-target specimen.

18 Claims, 17 Drawing Sheets

(56) References Cited

U.S. PATENT DOCUMENTS

| | | | |
|---|---|---|---|
| 5,700,692 A * | 12/1997 | Sweet | 436/50 |
| 5,760,900 A | 6/1998 | Ito et al. | |
| 5,851,835 A | 12/1998 | Groner | |
| 5,956,139 A | 9/1999 | Meyer et al. | |
| 6,091,492 A | 7/2000 | Strickland et al. | |
| 6,890,487 B1 | 5/2005 | Sklar et al. | |
| 7,024,316 B1 * | 4/2006 | Ellison et al. | 702/45 |
| 7,245,379 B2 | 7/2007 | Schwabe | |
| 7,392,908 B2 * | 7/2008 | Frazier | 209/3.1 |
| 7,855,078 B2 * | 12/2010 | Evans | 436/63 |
| 7,943,384 B2 * | 5/2011 | Durack et al. | 436/63 |
| 8,206,987 B2 * | 6/2012 | Durack et al. | 436/63 |
| 8,211,629 B2 * | 7/2012 | Schenk et al. | 435/2 |
| 2002/0170365 A1 | 11/2002 | Sklar et al. | |
| 2003/0032193 A1 | 2/2003 | Narisada | |
| 2003/0058445 A1 | 3/2003 | Fritz et al. | |
| 2003/0180955 A1 | 9/2003 | Ozasa et al. | |
| 2004/0260157 A1 | 12/2004 | Montes | |
| 2005/0180887 A1 | 8/2005 | Sklar et al. | |
| 2006/0052583 A1 | 3/2006 | McCausland | |
| 2006/0256336 A1 | 11/2006 | Fritz et al. | |
| 2007/0240496 A1 | 10/2007 | Farrell | |
| 2008/0292500 A1 | 11/2008 | Sklar et al. | |
| 2009/0107893 A1 | 4/2009 | Schembri et al. | |
| 2009/0275073 A1 * | 11/2009 | Shioyama | 435/29 |
| 2011/0005978 A1 | 1/2011 | Bohm et al. | |
| 2011/0045995 A1 | 2/2011 | Sklar et al. | |
| 2011/0312536 A1 | 12/2011 | Sklar et al. | |
| 2012/0097582 A1 | 4/2012 | Tsukii et al. | |

FOREIGN PATENT DOCUMENTS

| | | |
|---|---|---|
| JP | 8-12146 | 2/1996 |
| JP | 8-201268 | 8/1996 |
| JP | 2966057 | 8/1999 |
| JP | 2001-183382 | 7/2001 |
| JP | 2002-303633 | 10/2002 |
| WO | WO 02/16227 A1 | 2/2002 |
| WO | WO 2004/026340 A1 | 4/2004 |

OTHER PUBLICATIONS

Supplementary European Search Report issued Aug. 29, 2012, in Patent Application No. 05734713.0.

Gregory J. McClune, et al., "A Simple System for Mixing Miscible Organic Solvents With Water in 10-20 ms for the Study of Superoxide Chemistry by Stopped-Flow Methods", Biophys. J., vol. 24, No. 1, XP 55035775, Oct. 1, 1978, pp. 65-69.

Official Communication Pursuant to Article 94 (3) EPC issued on Apr. 4, 2013 in the corresponding European Patent Application No.: 05 734 713.0.

* cited by examiner (a)

(b)

$r < \alpha < L/2$

METHODS OF SEPARATING, IDENTIFYING AND DISPENSING SPECIMEN AND DEVICE THEREFOR, AND ANALYZING DEVICE METHOD

CROSS-REFERENCE TO RELATED APPLICATIONS

This application is a continuation of U.S. Ser. No. 11/587,210 filed Apr. 17, 2007, the entire contents of which are incorporated herein by reference, and is based upon and claims the benefit of priority from International Application No. PCT/JP2005/07848 filed Apr. 25, 2005, which claims priority under 35 U.S.C. 119 to Japanese Application Nos. 2004-128467 filed Apr. 23, 2004 and 2004-280187 filed Sep. 27, 2004.

TECHNICAL FIELD

This invention relates to a method for separating, identifying and dispensing a specimen (condensed specimen) and apparatus and an analyzing device for executing each method.

TECHNICAL BACKGROUND

A conventional cell sorter which is used for separating, identifying and dispensing a specimen roughly comprises a separating device, a detection device and a dispensing device.

Described below is an explanation of a separating device with reference to FIG. 41. First, a test tube 241 is vibrated or inside of the test tube 241 is stirred in order to unify a condensed specimen 243 in the test tube 241. Then, the condensed specimen 243 in the test tube 241 is repeatedly conducted a process of suction/ejection 251 with a pipette 245. Since the condensed specimen 247 receives a shear stress through the repetition of the suction/ejection 251, the specimen will be separated into single specimen 249. In this manner, a single specimen located at the surface side of the condensed specimen 247 is tend to be subjected to shear stress, which is easily to be separated into the single specimen 249. However, a single specimen located in the center of the condensed specimen 247 is always subjected to high pressure until the separation of the condensed specimen 247 is completed.

Next, described below is an explanation of a detection device with reference to FIG. 42. When a container storing a separated specimen 211 is applied a pressure such as pressurized air 215 in a detection device 201, the specimen 211 flows into a nozzle from its outlet/inlet 214 and goes up through the nozzle. The specimen 211 flew into the outlet/inlet 214 of the nozzle is irradiated by a monitor light 203, and this irradiation generates a fluorescent/scattered light 205. Each specimen is judged by detecting this fluorescent/scattered light 205. At that time, a sample flow 207 including the specimen 211 is surrounded by a sheath flow 209, while the flow speed of the sample flow 207 and the sheath flow 209 are controlled such that the width of sample flow 207 is within a certain range so as to let the specimen 211 flow one by one. This is for the purpose that each specimen is exposed to the monitor light 203.

Described below is an explanation of a dispensing device with reference to FIG. 43. A specimen is dispensed in a dispensing device 221. First, a specimen is applied supersonic vibration in an ejecting device 223 to form liquid droplets. Then, for example, a several hundreds volts of charge is applied to the liquid droplets 225 formed by supersonic vibration.

Then a several hundreds volts of electric pressure is applied through a deflection plate 227 to liquid droplets to dispense it into containers 233,235, while the direction of dropping each liquid drop is separated to a positive pole side 229 and a negative pole side 231. Nonpatent Reference 1: T. Yamashita et al., Cell Technology Vol. 16. No. 10 pp 1532-1541, 1997

DISCLOSURE OF THE INVENTION

Problem to be Solved by the Invention

The conventional cell sorter comprises a separating device, detection device and dispensing device as described above, and has problems as followings:

First, that all processes of vibrating a test tube, stirring the inside of test tube and sucking/ejecting through a pipette are manually conducted in the conventional separating device, so that there are lacking of quantitative reliability, reproducibility and effective separation. Additionally, since it is impossible to check the condition of separation, secure separation into single specimens cannot be checked.

Next, in the conventional detection device, the monitor light 203 is irradiated from the outside of the flow path to the specimen 211 and the generated fluorescent/scattered light 205 is received at the outside of the flow path. This condition decreases the irradiation effect of the monitor light 203 and the light reception sensitivity of the fluorescent/scattered light 205.

Furthermore, a distance 213 between a sample sucking device and a measuring point is long, so that a great deal of samples as much as several ml is required for measurement.

In addition, the specimen is subject to high-frequency oscillation or high charge such as several thousands volts when dispensing in the conventional dispensing device. Accordingly, when a living cell is used as a specimen, the death rate of the specimen after dispensing is high and even though the specimen is alive, the normal condition of the specimen is not guaranteed.

Means for Solving Problem

In a first aspect of the present invention to resolve the above-discussed problems, there is provided a specimen separating device comprising a container for storing a specimen;
a nozzle for sucking and ejecting the specimen from the foregoing container; a nozzle operating means for moving the nozzle vertically and laterally; and a nozzle controlling means for controlling the suction force and ejection force of the foregoing nozzle.

In a second aspect of the present invention, there is provided the specimen separating device according to the first aspect 1, further comprising a monitoring light irradiating device and a light receiving device for identifying the presence of identifier of the specimen that is passing through the foregoing nozzle or effect of the light.

In a second aspect of the present invention, there is provided a specimen separation method comprising a suction process for sucking a specimen through a nozzle from a container storing the specimen while controlling suction force in accordance with data; an ejection process for ejecting the sucked specimen through the nozzle to a container with controlling ejection force in accordance with data; and a separation process for separating the specimen by crushing the specimen against an internal surface of the container, wherein in order to separate the specimen, each process is repeated to generate a shear stress to the specimen and the specimen is crushed against the internal surface of the container to generate a tensile stress.

In a forth aspect of the present invention, there is provided the specimen separation method according to the third aspect, wherein the foregoing specimen is irradiated by a monitor light and then separated while measuring the variation of the monitor light reflected by the foregoing specimen is measured.

In a fifth aspect of the present invention, there is provided a specimen identification device comprising a specimen introduction nozzle for contacting an end of the nozzle to a sample including a specimen which exists in a specimen source to introduce foregoing sample to another end; a flow path for forming an appropriate flow of foregoing sample supplied from the other end to identify an identifier of foregoing specimen, of which a part is inserted the other end of foregoing introducing; and an identification portion providing a light receiving portion for detecting foregoing identifier of the specimen by the light with a part of circumference of foregoing flow path.

In a sixth aspect of the present invention, there is provided the specimen identification device according to the fifth aspect further comprising a moving device that moves vertically and laterally at least one of the foregoing specimen introduction nozzle, the foregoing flow path, the foregoing measuring portion, or the foregoing specimen supply source.

In a seventh aspect of the present invention, there is provided the specimen identification device according to the fifth aspect or the sixth aspect, wherein the foregoing specimen supply source comprises a plurality of sample containers and sample supply nozzles, at least one of the foregoing plurality of sample containers stores the foregoing specimen, other containers store liquid, and the foregoing plurality of sample supply nozzles are connected each other, which is coupled to the foregoing one end of the foregoing specimen introduction nozzle.

In an eighth aspect of the present invention, there is provided the specimen identification device according to the fifth aspect or sixth aspect, wherein the foregoing specimen supply source comprises a plurality of sample supply nozzles, at least one of that is passed through liquid containing the foregoing specimen, at a merge position or vicinity of that where the liquid passing through each of the foregoing plurality of sample supply nozzles, at least one of a concave position or convex position for generating turbulent flow is provided, of which downstream is coupled to the foregoing one end of the foregoing specimen introduction nozzle.

In a ninth aspect of the present invention, there is provided a specimen identification method, wherein the foregoing specimen is passed with being decentered from the center of a fine flow path at an identifying area for identifying an identifier of the specimen passing through the foregoing fine flow path.

In a tenth aspect of the present invention, there is provided a specimen identification method, wherein a specimen being measured is introduced with being rotated in the identifying area for identifying an identifier of the specimen flowing in a fine flow path.

In an eleventh aspect of the present invention, there is provided a specimen identification method, wherein a specimen being measured is introduced in a flow path, a light variation from the foregoing specimen is measured, and an identifier of the specimen is identified based on a measurement result.

In a twelfth aspect of the present invention, there is provided a specimen identification method according to the eleventh aspect, wherein the foregoing light from the foregoing specimen is at least one or more fluorescence/transmitted light or scattered light, the identifier of the specimen is identified based on the foregoing light.

In a thirteenth aspect of the present invention, there is provided the specimen identification method according to the eleventh aspect or the twelfth aspect, wherein the foregoing light from the foregoing specimen is received by an optical fiber that has an optic axis tilting to the plane where is perpendicular to the central axis of the foregoing flow path in a part of circumference of the foregoing flow path.

In a fourteenth aspect of the present invention, there is provided the specimen identification method according to the eleventh aspect or the twelfth aspect, wherein a light receiving device with an optical fiber for irradiating a monitor light to the foregoing specimen is provided at a part of the foregoing flow path circumference, of which at least one of a part of the foregoing monitor light area with respect to the rectilinear direction is covered by a light blocking element.

In a fifteenth aspect of the present invention, there is provided the specimen identification method according to the eleventh aspect or the twelfth aspect, wherein a front end of an optical fiber, provided such that the front end is exposed at the wall of the foregoing flow path, receives the foregoing light from the foregoing specimen.

In a sixteenth aspect of the present invention, there is provided the specimen identification method according to eleventh aspect to the fifteenth aspect, wherein the foregoing light is received at a front end of the optical fiber, of which the end shape of a core is square, and opposing two sides of the foregoing square in the foregoing core is arranged along with the foregoing flow path.

In a seventeenth aspect of the present invention, there is provided the specimen identification method according to the sixteenth aspect, wherein the width between rest two sides of the foregoing square, extending in the direction crossing the foregoing flow path, is larger than the width of the foregoing flow path.

In an eighteenth aspect of the present invention, there is provided the specimen identification method according to the eleventh aspect or the twelfth aspect, wherein the foregoing specimen in the foregoing flow path is irradiated by the monitor light from a monitor light irradiating device, and the center of an end of an optical fiber for receiving the light is aligned with the side with respect of the rectilinear direction of the foregoing monitor light.

In a nineteenth aspect of the present invention, there is provided the specimen identification method according to the eighteenth aspect, wherein the foregoing end of the foregoing optical fiber is aligned such that the foregoing center is within a range of 45-135 degree or 225-315 degree with respect to the foregoing monitor light rectilinear direction.

In a twentieth aspect of the present invention, there is provided the specimen identification method according to the eleventh aspect or the twelfth aspect, wherein the foregoing specimen in the foregoing flow path is irradiated by the monitor light from a monitor light irradiating device, an optical fiber for receiving the light is provided, so as to being arranged off from either upstream or downstream of the foregoing flow path with respect to the foregoing monitor light rectilinear direction.

In a twenty-first aspect of the present invention, there is provided the specimen identification method according to the eleventh aspect or the twelfth aspect, wherein the foregoing specimen being measured is introduced in the foregoing flow path, an optic axis is set on a plane which is perpendicular to the foregoing specimen traveling direction and the foregoing specimen is irradiated by the monitor light from a plurality of points.

In a twenty-second aspect of the present invention, there is provided the specimen identification method according to the eleventh aspect or the twelfth aspect, wherein a variation in two or more elements of the foregoing light from the foregoing specimen that is obtained by irradiating the monitor light is measured at the same time, based on the measurement result, and the identifier of the specimen is identified.

In a twenty-third aspect of the present invention, there is provided the specimen identification method according to the eleventh aspect to the twenty-second aspect, wherein a variation pattern including arbitrary value and varying length of time based on the foregoing light obtained from the foregoing specimen is measured.

In a twenty-fourth aspect of the present invention, there is provided a specimen identification method, wherein a specimen being measured is introduced in a flow path, a monitor light is irradiated to the foregoing specimen, a light information from the foregoing specimen obtained by irradiating the monitor light is measured in at least one or more light receiving device which is different from a plane, the foregoing plain is perpendicular to the foregoing specimen traveling direction and includes the optic axis of the foregoing monitor light, and the identifier of the specimen is identified based on a measurement result.

In a twenty-fifth aspect of the present invention, there is provided a specimen identification method, wherein a light information from a specimen obtained by irradiating the monitor light is measured at a inner wall of the flow path located in an area of ±45 degree or more with respect to specimen traveling direction while setting a center as the central point of flow path in a plane, the foregoing plane is perpendicular to the specimen traveling direction and includes an optic axis of the monitor light.

In a twenty-sixth aspect of the present invention, there is provided the specimen identification method, wherein the foregoing specimen is irradiated by the foregoing monitor light without concentration.

In a twenty-seventh aspect of the present invention, there is provided a specimen dispensing device for dispensing a specimen, identified as a target specimen or a non-target specimen by the identifying device, to the target specimen and the non-target specimen respectively, comprising a dispensing nozzle for forming liquid droplets containing specimen at its front end; a collecting container for collecting liquid droplets containing the target specimen from the foregoing liquid droplets by introducing it; a drain tank for collecting liquid droplets containing the non-target specimen from the foregoing liquid droplets by introducing it; and a moving means for moving at least one of the foregoing collecting container, the foregoing drain tank or the foregoing dispensing nozzle while forming the foregoing liquid droplets.

In a twenty-eighth aspect of the present invention, there is provided the specimen dispensing device according to twenty-seventh, wherein the foregoing dispensing nozzle is located such that its front end is coming to contact the liquid in the foregoing collecting container or the foregoing drain tank.

In a twenty-ninth aspect of the present invention, there is provided the specimen dispensing device according to the twenty-seventh to the twenty-eighth aspect, wherein the foregoing dispensing nozzle is located such that its front end is coming contact a wall surface of the foregoing collecting container or the foregoing drain tank.

In a thirtieth aspect of the present invention, there is provided a specimen dispensing method, wherein by using at least one selected from the foregoing specimen identifying device or the foregoing specimen identifying device, a target specimen and a non-target specimen is identified based on a light information obtained from the specimen in the foregoing identifying device, when the target specimen and the non-target specimen are dispensed into a collecting container and a drain tank respectively based on the foregoing light information and a flow velocity of the specimen, such that liquid droplets or liquid flow containing the specimen continuously flow from the dispensing nozzle to a liquid level of the collecting container and the drain tank, and dispensing and disposing of the target specimen or the non-target specimen is carried out.

In a thirty-first aspect of the present invention, there is provided a specimen flow velocity measuring method, wherein at least one or more specimen being measured is introduced in a flow path, a light information from the specimen is measured by light receiving devices that are located in at least two or more different positions with respect to the foregoing specimen traveling direction, and a flow velocity is measured based on the light information obtained by each light receiving devices and spaces among each light receiving devices.

In a thirty-second aspect of the present invention, there is provided the specimen flow velocity measuring method according to the thirty-first aspect, wherein a monitor light is irradiated from two or more different positions with respect to the foregoing specimen traveling direction, light information obtained from the foregoing specimen by irradiating the foregoing monitor light is measured at each light receiving devices which are located in a plane, the foregoing plane is perpendicular to the specimen traveling direction and includes an optic axis of the monitor light, a flow velocity is measured based on time differences of light information obtained by each light receiving device and spaces among each light receiving device.

In a thirty-third aspect of the present invention, there is provided a specimen dispensing method, wherein by using at least one selected from the foregoing specimen identifying device or the foregoing specimen identifying device, a target specimen and a non-target specimen is identified based on light information obtained from a specimen in the foregoing identifying device, while measuring a flow velocity of the specimen by a specimen flow velocity measuring method according to the aspect thirty-first or thirty-second, the target specimen is dispensed and the non-target specimen is disposed of based on the flow velocity of the specimen, a result of identification and a calculated result of an arrival time from the foregoing identifying device to the front end of the foregoing dispensing nozzle.

In a thirty-fourth aspect of the present invention, there is provided the specimen dispensing method according to the aspect thirtieth to the thirty-third aspect, wherein a target specimen and a non-target specimen is identified based on light information obtained from a specimen in the foregoing identifying device, while measuring a flow velocity of the foregoing specimen, a result of identification and an arrival time from the foregoing identifying device to a front end of the foregoing dispensing nozzle is calculated, such that a moving member for changing relative position for the foregoing collecting container, the foregoing drain tank, and the foregoing dispensing nozzle is provided in at least either one of the foregoing dispensing nozzle, the foregoing collecting container, or the foregoing drain tank, such that liquid droplets or liquid flow containing the target specimen at the front end the foregoing dispensing nozzle is dispensed to the collecting container, liquid droplets or liquid flow containing the non-target specimen is dispensed to the drain tank by specimen delivery pressure.

In a thirty-fifth aspect of the present invention, there is provided the specimen dispensing method according to either one of the aspect thirtieth, thirty-third or thirty-fourth, wherein when the foregoing dispensing nozzle is in normal condition, a relative position between the foregoing nozzle and the foregoing drain tank is adjusted such that the liquid flow running from the foregoing dispensing nozzle flow continuously in contact with the liquid of the foregoing drain tank, in dispensing condition where the target specimen being dispensed is sensed, the relative position between the foregoing dispensing nozzle and the foregoing drain tank is changed, after liquid flow or liquid droplets flowing from the foregoing dispensing nozzle is separated from the liquid in the foregoing drain tank, the relative position between the foregoing dispensing nozzle and the foregoing collecting container is changed such that the liquid flow or the liquid droplets containing the foregoing the target specimen is dispensed to the foregoing collecting container, and after the foregoing target specimen is dispensed to the foregoing collecting container, the foregoing dispensing nozzle is returned to the foregoing normal condition.

In a thirty-sixth aspect of the present invention, there is provided the specimen dispensing method according to the thirty-fifth aspect, wherein the foregoing dispensing nozzle carries out disposing of liquid or dispensing by letting at least its front end curved line reciprocate movement between the foregoing drain tank and the foregoing collecting container.

In a thirty-seventh aspect of the present invention, there is provided the specimen dispensing method according to either one of the thirtieth aspect, the thirty-third to the thirty-fifth, wherein a front end the foregoing dispensing nozzle is located in the liquid in the foregoing drain tank or the liquid in the foregoing collecting container to carries out disposing of or dispensing liquid.

In a thirty-eighth aspect of the present invention, there is provided the analyzing device further comprising at least either one of the foregoing specimen separating device or the foregoing specimen identifying device, or the foregoing specimen dispensing device.

In a thirty-ninth aspect of the present invention, there is provided the analyzing device according to the thirty-eighth aspect further comprising a controlling means for controlling operations of each device.

In a fortieth aspect of the present invention, there is provided the specimen separation/identification/dispensing method, wherein each device of the foregoing specimen separating device, foregoing specimen identifying device, or the foregoing specimen dispensing device is controlled fully-automatically.

In a forty-first aspect of the present invention, there is provided the sterilizing method includes at least one of the foregoing specimen separating device, the foregoing specimen identifying device or the foregoing specimen dispensing device, wherein the inside of the device and the specimen, gas or liquid flow path is sterilized by using sterilizing gas.

Effect of the Invention

A specimen separating device and the method thereof of the present invention separates a condensed specimen by crushing the specimen against internal surface such as bottom and side surfaces of a container while adjusting the position of a nozzle for sucking/ejecting the specimen, which enables the condensed state specimen to be separated into groups of small condensed specimens (or single specimen) by applying a most appropriate shear stress, without applying extra stress. As a result, the number of times of suction/ejection operation is optimized and the specimen can be separated without being subjected to extra stress.

Moreover, the separation of the specimen can be conducted while monitoring the size of the specimen, so that at the point where the condensed state specimen turned into an arbitrary condensed state, for example, at the point where it is separated into a single specimen, the separation may be finished. Accordingly, unnecessary specimen separation is omitted, the number of times of suction/ejection operation is optimized and the specimen can be separated without being subjected to extra stress.

A specimen identifying device and the method thereof of the present invention can irradiate a direct monitor light from the wall of a flow path and receive the fluorescence/transmitted light, so that monitor light irradiation efficiency and light reception efficiency for a fluorescence/transmitted light can be improved. In addition, the capability of miniaturization of the specimen identifying device enables a small quantity of sample containing the specimen to be identified the specimen. Furthermore, a plurality of containers storing a sample containing the specimen, and at least one of the sample stored in the containers includes the specimen, and by storing samples not including the specimen in other containers, flowing samples into the specimen identifying device is possible even in the case that the sample containing the specimen is small amount to identify specimens.

A specimen dispensing device and the method thereof of the present invention, the flow velocity of the specimen in the identifying device is measured to calculate an arrival time of the specimen from there to the front end of the dispensing nozzle, an operation of a collecting container based on the timing of the specimen arrival to the end of the dispensing nozzle is possible. Accordingly when a specimen needed to be collected flows, the collecting container is operated to collect it, and when a flowing specimen is not needed to be collected, disposing of it to a container for waste liquid is possible. Therefore, the specimen is not subjected to extra stress such as high-frequency vibration or several thousands volts of high charge as the case in prior art. Additionally, the front end location of the dispensing nozzle can be controlled, and the condition of liquid droplets or liquid flow containing the specimen from the dispensing nozzle can be controlled. Hence, it is possible to permit flow liquid droplets or liquid flow containing the specimen from the dispensing nozzle into the collection container or waste liquid tank. Consequently, the death rate of the specimen after dispense decreases and collected with being normal condition, besides high speed dispensing can be achieved since dispensing and disposing are conducted without waiting for liquid droplets formation.

In the present invention, a combination of the specimen separating device, the specimen identifying device and the specimen dispensing device, in the case that a single cell is collected from a cell aggregation from a cell stem, as described above, the single cell is collected from a cell aggregation without being damaged the stem. Also, it is possible to carry out a process of collecting the single cell from the cell aggregation automatically, by controlling conditions of each device in interlocking way.

Figure 1:
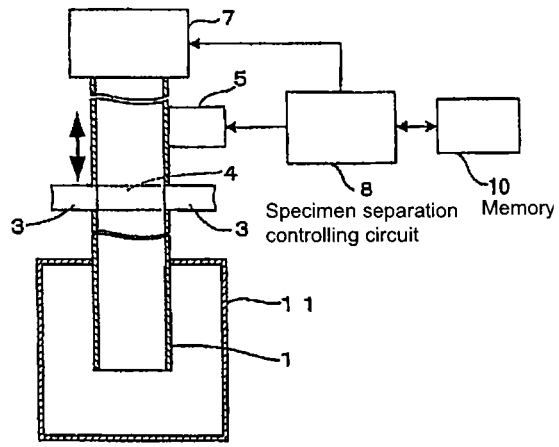
FIG. 1 is a cross section diagram of a specimen separating device related to an embodiment of the present invention.

DESCRIPTION OF THE REFERENCE NUMERALS 1 nozzle
3 optical fiber
4 monitor light
5 nozzle operating means
7 suction/ejection force controlling means
9 specimen
11 container
13 tension
15 collision force
17 distance
18 optic connector
19 shear stress
21 specimen
23 ejection
25 suction
31, 31a, 31b, 32, 36a, 36b, 38 optical fiber
31c core
33 monitor light
35 transmitted light
37 fluorescence
39 the sample flow
40 laminar flow aperture
41 sheath flow
42 velocity gradient
43 distance
45 specimen introduction nozzle
47 pressure air
48 elevation
49 sample
51 fine flow path
52 wall
53 suction/ejection opening
55 pressure
57 pressure
61 nozzle moving means
63 non-target specimen
65 target specimen
67 liquid droplets
69 drain tank
71 sliding direction
72 solution
73 container
81, 83, 85, 87 sample
89, 91, 93, 95 flow path
90 sample
97, 99, 101, 103 pressure
111 air pressure
113 nozzle
115, 117 container
119 driving
121, 123, 131 member
133, 135, 137, 139 container
141, 143 driving
151 merging point
153, 157 branch nozzle
155, 159 liquid for suspending the specimen
161 concaved portion
163 turbulent flow
201 detection device
203 monitor light
205 fluorescence/scattered light
207 sample flow
209 sheath flow
211 specimen
213 distance
214 nozzle outlet/inlet
215 pressurized air
221 dispensing device
223 ejecting device
225 liquid droplets
227 deflection plate
229 positive pole side
231 negative pole side
233, 235 container
241 test tube
243 condensed specimen
245 pipette
247 condensed specimen
249 single specimen
251 suction/ejection
301 analyzing device
311 separating device
313 nozzle operating means
315 nozzle
331 rotating base
333 container
335 rotating means
337 moving means
339 filter
351 identifying device
353 moving means
355 light irradiation optical fiber
357 light receiving optical fiber
359 suction nozzle
371 dispensing device
373 nozzle moving means
375 dispensing nozzle
377 drain tank
379 sliding means
391 container
393 well
397 moving means
400, 402, 404, 406 optical fiber

THE BEST MODE FOR CARRYING OUT THE CLAIMED INVENTION

Preferred embodiment of the present invention will be explained hereinafter with reference to the drawings. In the present invention, a specimen refers to a particulate matter, for example, organic matter such as cell or inorganic matter like polystyrene, foam forming material and magnetic material, or metal and other material as large as from about 0.1 μm to 500 μm, or a condition that these materials are suspended in liquid. A specimen also indicates the one labeled the presence or the level of its identifier, or the one spontaneously irradiates. In this case, a specimen may be labeled with a combination of a plurality of presences of identifier or levels, or a plurality of specimens with multiple types of labeling element may be exist. And a condensed specimen refers to a material as large as around 0.1 μm to 10 mm which is condensed said specimen, or a condition that these materials are suspended in a liquid. An analysis of a specimen is conducted via steps of separating a single specimen from condensed specimen, identifying the separated specimen, and dispensing the identified specimen by use of devices described below.

Now, a method of separating, identifying and dispensing specimen and device thereof, which is applied for an analyzing device of minute objects, is explained in subsequence.

(Specimen Separation)

Figure 2:
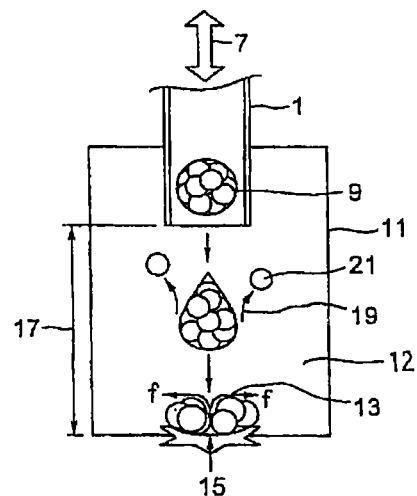
FIG. 2 is a diagram for explaining an operation of the specimen separating device related to an embodiment of the present invention.
Figure 3:
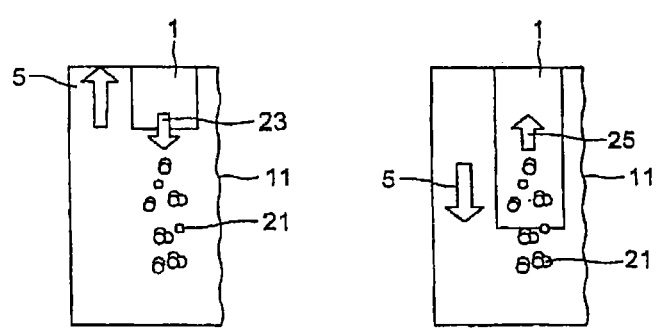
FIG. 3 is a structural diagram of a stirring device related to an embodiment of the present invention.

First, one embodiment of specimen separation related to the present invention will be explained in reference to FIG. 1. The separation comprises separation and stirring. A cylinder shaped nozzle 1, immersing its lower end in the solution containing a specimen in a container 11 as shown in FIG. 2 and FIG. 3, is used to suck or eject the specimen in the solution. The nozzle 1, made of such as stainless, is mounted to the nozzle operating means to move the nozzle 1 vertically and laterally. A suction/ejection controlling means 7 for controlling the suction/ejection force to suck the specimen into the nozzle 1 or eject the specimen from the nozzle 1 is also mounted to the nozzle 1. The suction/ejection condition of the suction/ejection controlling means 7 and the movement condition of the nozzle 1 of the nozzle operating means 5 are controlled by a specimen separation control circuit 8. A pair of optical fibers 3 are oppositely disposed on a wall of the nozzle 1, according to need, which forms a structure that one optical fiber 3 irradiates a monitor light 4 and another optical fiber 3 receives the light to detect the presence or the level of the identifiers of the specimen flow in the nozzle 1.

The specimen separation method is explained with reference to the pattern diagram of FIG. 2.

A condensed state specimen 9 in the nozzle 1, of which the lower end is immersed into the solution containing the specimen in a container 11, is ejected from the nozzle 1 by means of said suction/ejection controlling means 7 to be crushed the wall of container 11 such as bottom or side wall. FIG. 2 illustrates a case of crushing the specimen against the bottom surface of the container 11. The condensed state specimen (cell aggregation) 9 crushed against the bottom surface of the container 11 is carried out the first time separation by tensile stress 13 generated by the crush. Repeating this suction/ejection step several times if required completes the process of separation. To separate the specimen 9 from condensed state to arbitrary condensed state, the number of repetition of suction/ejection and tension 13 should be controlled. The number of repetition can be controlled through observation of the condensed state of specimen 9 by use of the optical fibers 3 and the monitor light 4 shown in FIG. 1, when necessary. And tension 13 can be controlled through adjustment of a distance 17 from a front end of nozzle 1 to the bottom surface of the container 11 that is adjusted by the height of the nozzle through nozzle operating means 5, and of ejection force adjusted by the suction/ejection force controlling means 7. Adjusting the number of repetition of suction/ejection and tension 13 enables specimen to be separated into the arbitrary condensed state in the short period of time under the best condition without having extra stress. Excessive stress may damage the specimen 9.

Above mentioned observation of the specimen is to measure the light information from the specimen obtained by irradiating the monitor light to the specimen through the optical fibers 3 shown in FIG. 1. The light information refers to mainly the presence or the level of the identifier, and for example, size, refraction index, reflectivity, magnetic susceptibility, intensity of electric field or magnetic field of the material, electro magnetic waves such as electric wave, ultraviolet light and X ray, or wave length of fluorescence, or the presence or level of property such as electro magnetic waves of specimen itself or identifying agent contained by specimen. In addition, the light information includes results obtained by irradiating the monitor light to the specimen, or the specimen which spontaneously irradiates itself, for example, the presence or the level of transmitted light, scattered light (forward scattered light, side scattered light and backward scattered light), absorption, electro magnetic waves, wave range, fluorescence or the like are also included.

Electro magnetic waves includes the one spontaneously generated by specimen itself or identifying agent contained by the specimen as well as the one labeled by the effect of electro magnetic waves from the specimen or other than said labeling element (e.g., reflection, transmission, shielding, absorption, etc.)

It is preferred that the monitor light 4 used for observation of the specimen uses the light source such as laser light source, xenon lamp and xenon mercury lamp. The irradiation surface and the light receiving surface (measuring point) of the monitor light 4 are attached in the exposed condition at the internal surface of the nozzle 1 as same as described below in the explanation of the specimen identifying device. This is for the purpose of irradiating and receiving the monitor light much closer to the specimen.

Additionally, it is desired that the irradiation surface and the light receiving surface where is each end of a pair of optical fibers 3 are oppositely arranged so as to sandwich the specimen flow path, and the light path of the monitor light go from the irradiation surface through the center of the nozzle 1 to the light receiving surface. But when the specimen doesn't go through the center of the nozzle (flow path) 1 is not limited, the light path of the monitor light is set to pass the section where the specimen goes. That is, the light path of the monitor light in the nozzle 1 is determined in accordance with the section where the specimen goes, and this light path determines the forming position of irradiation surface and light receiving surface. The irradiation surface and the light receiving surface can be provided at the wall in multistage position in the direction of the flow path according to needs, which is not shown. This structure improves reliability and information amount, since double or triple measurement is carried out by using identical wave length. Or using different wave lengths obtains information corresponding to the wave length, results in a large amount of information.

Crushing the condensed state specimen 9 that was sucked by nozzle 1 and then ejected against the bottom surface of the container 11 by the ejection force results in the application of a collision force 15 from the bottom surface to the specimen 9. In this case, the distance 17 from the front end of the nozzle 1 to the bottom surface of the container 11 is controlled while adjusting the ejection force in accordance with the condense size of the specimen 9 (condensed state), so as not to applying extra stress more than the necessary force for separating the condensed state specimen 9 to the specimen 9. That means, in the case of separating the condensed state with being held the damage of the specimen 9 to the minimum, the repetition time of suction/ejection and the tension 13 as well as collision force 15 should be adjusted. In each case, controlling the ejection force by use of distance 17 and ejection force suction/ejection force controlling means carries out the measurement. Or, the distance 17, the ejection force and the repetition time can be automatically controlled with optimal conditions prepared in advance.

Furthermore, the specimen 9 ejected from the nozzle 1 is subjected to the shear stress 19 from the surrounding liquid 12 of the specimen 9, while being crushed against the bottom surface of the container 11, and then sucked into the nozzle 1. This shear stress 19 from the surrounding liquid 12 separates the condensed state specimen 9. In other word, in this specimen separating device, the specimen is separated not only due to the collision force and tension 13 generated by crush against the bottom surface of the container 11 but also due to the shear stress applied by the surrounding liquid 12 when sucking/ejecting the specimen into/from the nozzle 1. Since the shear stress varies on the pressure of the liquid 12, it is necessary to select an optimal condition of the distance 17 between nozzle 1 and the bottom surface of the container 11. And then, until the condensed state specimen 9 is separated into the arbitrary condensed state such as single state specimen 21, each process of sucking into the nozzle 1, ejecting from the nozzle 1 and crushing against the bottom surface of the container 11 is repeated.

The shape of the nozzle 1 is not limited, that is a pipe type means of which inside forms flow path to permit liquid flow, and it is desired that the irradiation surface and the light receiving surface of the optical fiber 3 can be exposed from its side. For example, the cross sectional shape of the nozzle 1 may be cylinder type, square, rectangular, and so on, without being limited. Regarding the internal surface of the nozzle 1, a simple form is shown in FIG. 2, but not limited to this form, and corrugation, wave-form or projections and the like can be formed to increase the specimen separation effect in the suction/ejection process.

Next, a stirring operation of the specimen arranged at the front stage of the specimen identifying device, where is at the back stage of the specimen separating device, according to needs, is explained with reference to FIG. 3. First, as shown in FIG. 3 (a), the front end of the nozzle 1 is immersed into the solution of the container 11 such that inside of the nozzle 1 contains the specimen 21. Then, an ejection 23 of the specimen 21 into the container 11 is conducted with the nozzle 1 being elevated by the ejected nozzle operating means 5.

And then, as shown in FIG. 3(b), a suction 25 process of a specimen 21 is conducted with the nozzle 1 being declined by the ejected nozzle operating means 5. After that, the specimen 21 is ejected with the nozzle 1 being elevated and sucked with the nozzle 1 being declined. Repeating this operation several times stirs the specimen 21 in the container 11. It is possible to disperse the specimen 21 uniformly in the container 11 by use of this method.

Since above mentioned conditions vary on the type of the specimen such as type of cell, as shown in FIG. 1, the specimen separation control circuit 8 stores in the memory 10 the separation conditions of each specimen as data, preobtained by experiments, and controls the suction/ejection force controlling means 7 and the nozzle operating means 5 based on the data.

(Specimen Identification)

Figure 4:
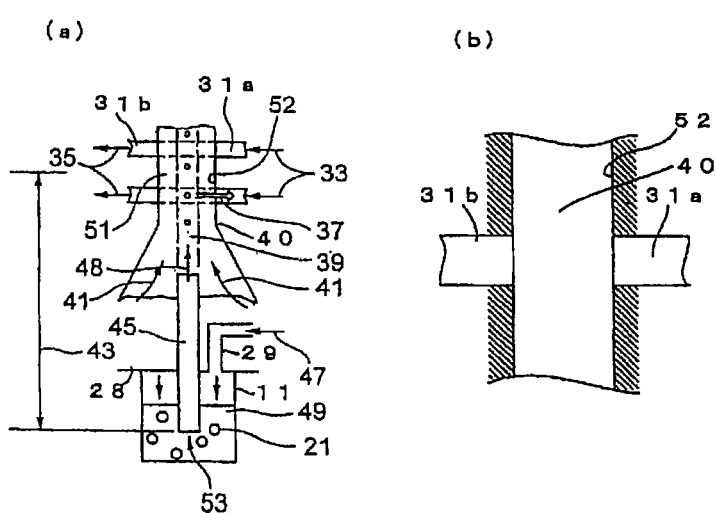
FIG. 4 is a structural diagram of an example of specimen identifying device related to an embodiment of the present invention.

Next, a specimen identifying device of the present invention is explained with reference to FIG. 4. The specimen identification roughly comprises the identification process and delivery process.

First, the specimen identifying device is explained. The specimen identifying device shown in FIG. 4(a) comprises a cover member 28 which covers the open end of the container 11, a gas introduction opening 29 provided at a part of the cover member 28, a specimen introduction nozzle 45 of which one end is inserted into the liquid state sample 49 in the container 11 through the cover member 28, a laminar flow aperture 40 into where another end of the specimen introduction nozzle 45 is inserted, and an optical fiber 31a for irradiating the detection light and an optical fiber 31b for receiving the detection light that are exposed from the inner wall 52 of the laminar flow aperture 40. The laminar flow aperture 40 is an aperture formed in the pipe or block, which has an inner diameter of about 0.1 mm measuring section and a taper section that expands downwardly, and into the lower side of taper section, a sheath forming liquid, such as water, is introduced downwardly. The taper section is inserted another end of the specimen introduction nozzle 45. The laminar flow aperture 40 and the specimen introduction nozzle 45 are formed by stainless or the like. The light irradiation surface of the optical fiber 31a for irradiating the detection light and the surface reception surface of the optical fiber 31b for receiving the detection light are attached so as to contacting a fine flow path 51, respectively, as shown in FIG. 4 (b).

Next, a delivery process is explained. As shown in FIG. 4 (a), pressurizing the inside of the container 11 by use of pressure air 47 lets the liquid state sample 49 containing the specimen 21 in the container 11 flow into a suction opening 53 of the specimen introduction nozzle 45 and go up inside of the specimen introduction nozzle 45, thereby leading that the sample runs sheath flow 41 at the taper section to form the sample flow 39 and rises. In the identifying section of the laminar flow aperture 40, the sample flow 39 containing the specimen 21 runs in the condition being surrounded by the sheath flow 41, which results in the fine flow path 51.

Next, an identifying process is explained. The identifying process is a process for identifying (observing) a specimen which is delivered through a delivery process. A sample 49 containing the specimen 21 is irradiated by a monitor light 33 by the optical fiber 31a for irradiating the detection light while running through the fine flow path 51 in the measuring section of the laminar flow aperture 40. At that moment, identifying the specimen 21 is possible by receiving fluorescence or transmitted light generated from the specimen with the optical fiber 31b for receiving the detection light. The monitor light 33 can be irradiated when the specimen 21 reaches at the measuring section, or constantly is irradiated. Furthermore, when the specimen 21 spontaneously irradiates the light without irradiating the monitor light 33, it is not necessary to irradiate the monitor light 33.

In the present invention, two optical fibers 31a, 31b which are oppositely arranged so as to sandwich the specimen flow path is defined as one measuring section, as a pair. The optical fibers 31a, 31b that forms the measuring section are provided so as to contact the fine flow path 51 as shown in FIG. 4 (b). By providing the optical fibers 31a, 31b on the wall 52 where the fine flow path 51 contact, the monitor light 33 is directly irradiated from the wall 52 to the specimen 21 without transmitting airspace and a transparent member, and moreover, the transmitted light 35 and fluorescence 37 is received without transmitting the airspace like the monitor light 33. Accordingly, forming such structure improves the irradiation efficiency of the monitor light and the reception efficiency of the fluorescence/transmitted light. FIG. 4(b) shows the condition which the optical fibers 31a, 31b are directly attached to the laminar flow aperture 40, but in the case that the optical fibers 31a, 31b are attached to the block, the block will be attached inside of the laminar flow aperture.

Figure 5:
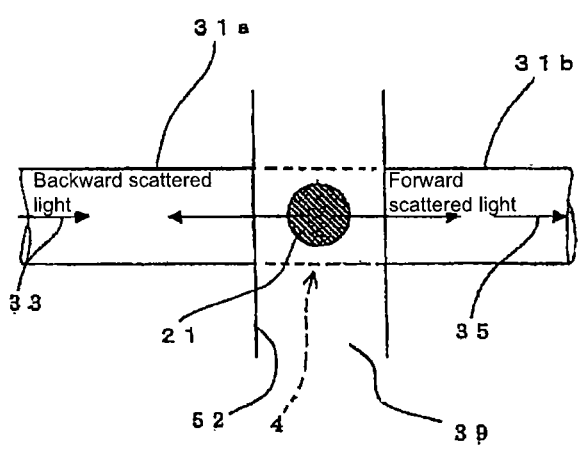
FIG. 5 is a diagram for explaining a scattered light generated by the specimen identifying device related to an embodiment of the present invention.
Figure 6:
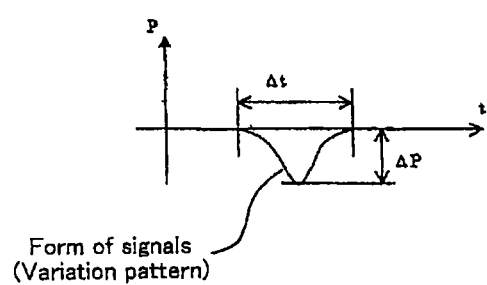
FIG. 6 is a wave form chart of detection signals acquired by the use of the specimen identifying device related to an embodiment of the present invention.

When the shape of the specimen 21 running in the sample flow 39 is measured, similar to the above mentioned measurement, the monitor light 4 is irradiated from the wall 52 to the specimen 21, and the transmitted light 35 or scattered light (forward scattered light, backward scattered light and side scattered light) from the specimen 21 can be used as shown in FIG. 5. In this case, the light irradiating device and the light receiving device of the optical fiber 31a,31b regarding the monitor light 33 (in FIG. 5, the light receiving device regarding transmitted light and the forward scattered light) are arranged so as to match the optic axis of each device, the specimen flow path which locates on the optic axis of the light irradiating device and the light receiving device is set as the measuring point of the specimen 21. Passing by the measuring point of the specimen 21 varies the amount of light received at the light receiving device (increases and decreases the amount of light received), so that by detecting the variation of the amount of light received, the shape of the specimen can be measured. For example, in the case that the specimen 21 is an impermeable material, when the specimen 21 passes by the measuring point, the loss of the amount of light received will be observed. And in another embodiment, in the case that transmitted light signals shown in FIG. 6 is detected, the shape and size can be identified from the change interval of the signal: $\Delta t$, peak value: $\Delta P$, and the shape of the waveform itself (variation pattern). In the light receiving device, the forward scattered light or transmitted light from the specimen is received, but using the transmitted light is less affected by the surface condition and capable of measuring the shape with better accuracy.

In the above description, the amount of light received variation of either forward scattered light or transmitted light regarding the monitor light was measured, by measuring both amount of light received, the shape of the specimen may be measured. Measuring the both amount of light received variation obtains more information regarding the shape of the specimen, so that more accurate shape measurement can be conducted.

Additionally, as shown in FIG. 5, while measuring the amount of light received variation of the transmitted light 35 by irradiating the monitor light 4 to the specimen 21, the amount of light received variation of the backward scattered light from the specimen 21 may be measured. To measure the backward scattered light, the light receiving device is set via nonreciprocal optical device at the irradiation side of the monitor light 4 (light source side of the monitor light 33), and at the light receiving device, the amount of light received variation is measured by transmitting the backward scattered light in the optical fiber 31a where the monitor light 33 is transmitted. In this case, other optical fiber than optical fiber 31a or light guide means may be used for transmitting the backward scattered light to the light receiving device. The nonreciprocal optical device transmits the light in one direction, not the light in the wrong direction.

As above mentioned, measuring both amount of light received variation of the transmitted light and the backward scattered light enables that the amount of light received variation measurement result of the transmitted light can be compensated by using the amount of light received variation measurement result of the backward scattered light, therefore, the specimen can be measured with better accuracy. For example, graphs in FIG. 7(a), (b) show the light reception power variation measurement results of the transmitted light of two identical sized specimen A, B.

As the graphs illustrate, even though the size of the specimen A, B is identical, the light reception power variation of the transmitted light can be different. For example, a loss of the sample A's transmitted light shown in FIG. 7(a) is 50% and the loss of the sample B's transmitted light shown in FIG. 7(b) is 20%. This is because the light reception power variation of the transmitted light is affected by the specimen condition (transmissibity, absorption, etc.).

From this reason, to detect (identify) the specimen condition, as in the example shown in FIG. 8(a), the light reception power variation of the backward scattered light generated by the sample A, B. In other words, from the light reception power variation measurement results of the backward scattered light, the specimen condition (transmissibility absorption, etc.) can be detected (identified). Utilizing the amount of light received variation measurement results of the backward scattered light to the amount of light received variation measurement results of the transmitted light, the shape of the specimen can be measured with better accuracy.

Figure 7:
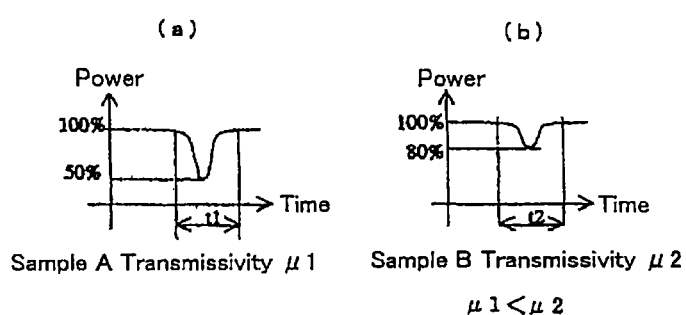
FIG. 7 is a first example wave form chart of the detection signals acquired by the use of the specimen identifying device regarding two specimens related to an embodiment of the present invention.
Figure 8:
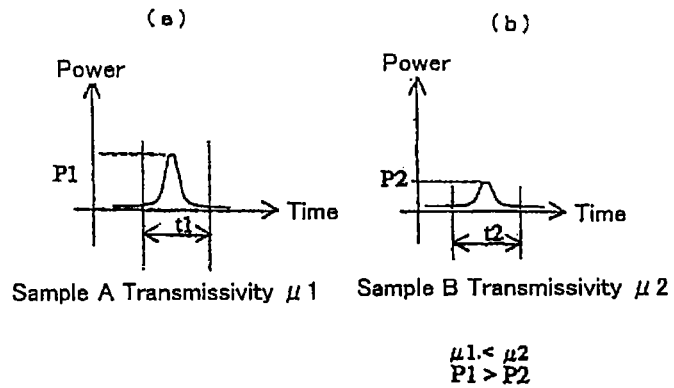
FIG. 8 is a second example wave form chart of detection signals acquired by the use of the specimen identifying device regarding two specimens related to an embodiment of the present invention.

Regarding each identifier of the sample A and the sample B, according to FIG. 7 and FIG. 8, the distribution of the scattered light forms the shape which compensates the distribution of the transmitted light. Accordingly, by determining its correlation with premeasured data accumulation, the result that the sample A and sample B is almost same size can be calculated.

In the above mentioned specimen measurement, the amount of light received variation's period and degree vary on the size, shape and condition of the specimen. That means, by measuring the amount of light received variation's period and degree, the size, shape, and so on of the specimen can be measured with accuracy. Since this measurement can be carried out even if the specimen is not labeled with fluorescence, etc. by use of the transmitted light. Therefore labeling burdens of the specimen with fluorescence, etc. can be omitted, which results in saving cost and so on. In addition, the shape of the specimen that cannot be labeled can be measured.

Moreover, when the size, shape and condition of the specimen is identified by the use of the amount of light received variation of the monitor light, the specimen of which the size, shape and condition is known is premeasured to prepare the amount of light received variation's period and degree. In other word, by measuring the amount of light received variation of the several kind of specimens that have different sizes, shapes and conditions, the degree of the amount of light received variation due to the specimen measurement is understood. By doing so, if an unknown size, shape and condition are measured, the size, shape and condition of the specimen can be measured with accuracy.

Additionally, in the specimen identifying device of the present invention, a light blocking effect member made of stainless copper, etc. may be used for the structure except the measuring section. Since the front ends of optical fibers 31a, 31b the are provided on the internal surface of the fine flow path, the monitor light 33 transmits only in the sample flow 39 containing the specimen. Thus, if the structure except the measuring section is formed by the light blocking effect member, it is advantageous because the effect of disturbance can be solved. For the specimen identifying device, whole fine flow path including the measuring section may be made of a material with high permeability such as glass and resin. In such case, it is proffered that wrapping the whole specimen identifying device with the member having light blocking effect if necessary, since the effect of disturbance can be solved.

The specimen identifying device of the present invention forms the cylinder shaped nozzle for sucking the specimen and the fine flow path for permitting the sheath flow and the sample flow, and is integrally formed with walls for providing the measuring section that has the optical fiber for irradiating or receiving the light of the monitor light for detecting the presence or the level of the identifier of the specimen. That is, as shown in FIG. 4(a), the device is comprised of the specimen introduction nozzle 45 for introducing a sample 49 to the other end by contacting one end to the sample 49 containing the specimen 21, the flow path into which the other end of the specimen introduction nozzle 45 is inserted, for forming the channel of the sample 49 flow supplied from the other end to be suitable for identifying the identifier of the specimen 21, and the identifying device of which optical fiber 31a for receiving the light to detect the identification of the specimen 21 by the light is provided at a part of the surrounding flow path. The flow path of this case corresponds to the laminar flow path 40 in FIG. 4(a), which is an aperture formed in the pipe or block, being comprised of the measuring section has an internal diameter of about 0.1 mm and the like, and the taper section expanding downwardly from there. Into the taper section, the other end of the specimen introduction nozzle 45 is inserted.

By forming the integral structure, a distance 43 between the measuring section and the nozzle 45 can be shortened. As a result, the identification judgment can be performed immediately after sucking the sample 49, so that even the small amount of sample, for example, several dozens µl order of sample amount can be measured. It is not necessary that the sample 49 is in the container 11, and the small quantity of sample can be put on the tray.

Also, in the specimen identifying device of the present invention, the light irradiating device of the monitor light 4 (optical fiber for irradiating the light) is not provided or provided at one section, contrary to the forward scattered light, backward scattered light, side scattered light or transmitted light, etc. from the specimen or the light receiving device (optical fiber for receiving the light) may be provided in the traveling direction of the specimen, with predetermined space, in multistage position. At that time, when the specimen itself spontaneously irradiates light, the formation doesn't require the installation of the light irradiating device, since the light information can be obtained without providing the light irradiating device.

Figure 9:
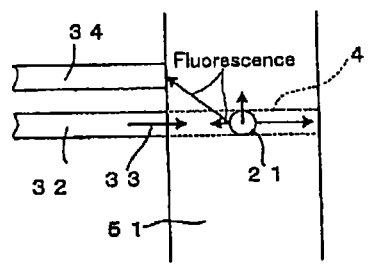
FIG. 9 is a lateral view showing a first and a second example of a positioning relationship among one position of the light irradiation and a plurality of positions of light reception for identifying specimen related to an embodiment of the present invention.
Figure 9:
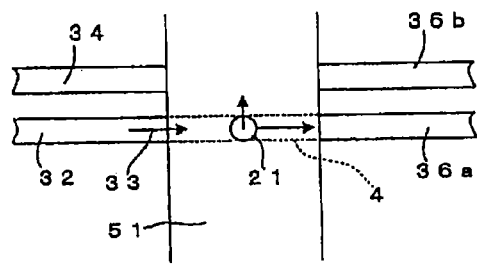

For example, as shown in FIG. 9(a), (b), the optical fiber 32 that is the light irradiating device of the monitor light 4 may be provided at one position, contrary to the optical fibers 34, 36a, 36b that are the light receiving devices may be provided at one or more positions. In FIG. 9(a), optical fiber 34 which is the light receiving device is provided on the optical fiber 32 for irradiating the light, and its light receiving surface contacts the fine flow path 51. Also, in FIG. 9(b), on the extended line of the optic axis of the optical fiber 32 for irradiating the light and at upper part of those, three optical fibers 34, 36a, 36b for receiving the light are arranged. The light receiving surfaces of the optical fibers 34, 36a, 36b for receiving the light are arranged in contact with the fine flow path 51. In this case, the optical fibers 34, 36b arranged above the optical fiber 32 for irradiating the light will be the light receiving device for receiving the fluorescence and the forward scattered light of the specimen 21.

When the specimen 21 is let flow in the fine flow path 51 in such specimen identifying device, monitor light variation at each stage's measuring point of the optical fiber 34, 36a, 36b will be detected in time difference. By using this time difference of the monitor light variation and the interval of the measuring point, the flow speed of the specimen 21 can be measured. The installation number of the light irradiating device and the light receiving device is not specially limited, so necessary devices can be provided. Also, providing position is not to be limited if the position can receive the transmitted light, scattered light and fluorescence.

Figure 10:
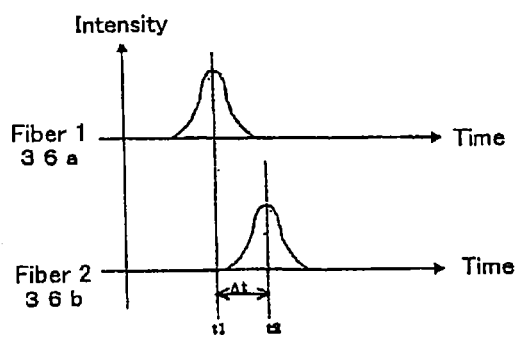
FIG. 10 is a wave form chart showing a variation in the strength of light reception at two positions of light reception for identifying specimen related to an embodiment of the present invention.

In addition, when multiply provided light receiving devices are adjacent each other, as shown in FIG. 9(a), (b), it is possible to let devices receive the light information from the specimen 21 at the same time on multiple locations. In this case, as shown in FIG. 10, as the specimen 21 runs inside of the fine flow path 51, the amount of light received at the optical fiber 36a in the lower stage, as well as the amount of light received at the optical fiber 34, 36 in the upper stage increases, and each peak value of the light received intensity can be obtained at the arbitrary time, with time difference. From this time difference of the peak value of the light received intensity at the optical fiber 34, 36a, 36b in the upper and lower stage and the interval of the optical fiber 34, 36a, 36b in the upper and lower stage, the flow velocity of the specimen 21 can be measured.

Figure 11:
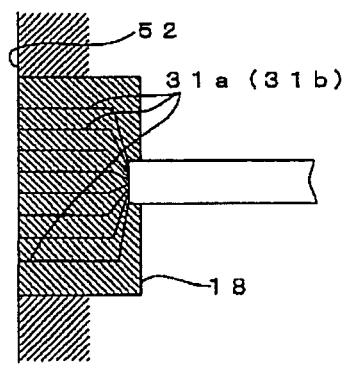
FIG. 11 is a cross section diagram showing an example of attachment of the optical fiber in the specimen identifying device related to an embodiment of the present invention.

Furthermore, when multiple optical fibers are used for irradiating or receiving the monitor light, as shown in FIG. 11, a multicore optical connector structure 18 may be attached to the side of the laminar flow aperture 40. In this case, optical fiber 22a, 22b for irradiating or receiving the light can be provided in the traveling direction of the specimen 21 with an accuracy of several µm or less. Moreover, when the eight-core optical connector is used, the installation with 1 µm of accuracy or less is possible.

As above mentioned, providing optical fiber for irradiating or receiving the monitor light with good accuracy makes possible to measure the flow velocity of the specimen with better accuracy. If the accurate measurement of the flow velocity is implemented, feedback controlling of this measurement result enables stable control of the flow velocity, thereby the reliability of the dispensing in the next process will be increased.

Figure 12:
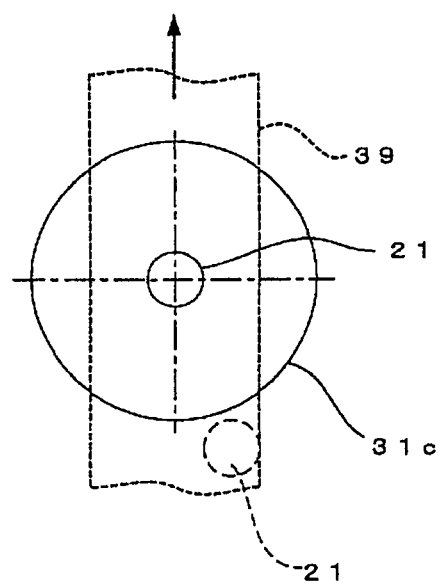
FIG. 12 is a whole view showing a general shape of an optical fiber core for receiving the light in the specimen identifying device related to an embodiment of the present invention.
Figure 13:
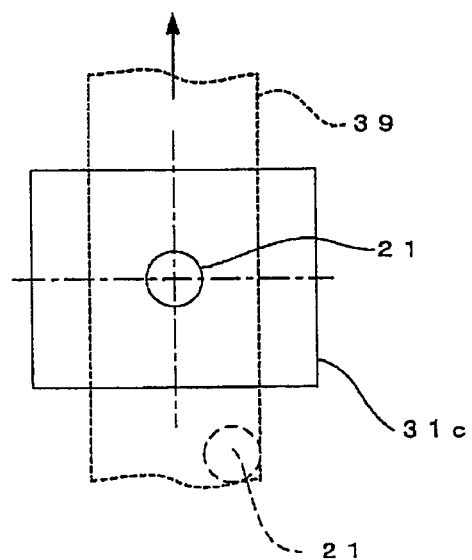
FIG. 13 is an end face view showing a preferred shape of the optical fiber core for receiving the light in the specimen identifying device related to an embodiment of the present invention.

It is preferred that one end of the core 31 of the optical fiber 31b which is used as the light receiving element of the transmitted light 35, which faces to the sample flow 39, is square shape like shown in the cross section diagram in FIG. 13 rather than circular shape like shown in the cross section diagram in FIG. 12. In this case, a pair of sides mutually opposed of the square core 31c end is arranged so as to be in perpendicular direction to the traveling direction of the sample flow 39, and the other pair is arranged so as to be in parallel direction to the traveling direction of the sample flow 39. The length of two sides extending in the lateral direction of the square is, for example, 50 µm when the width of the sample flow 39 is 30 µm. Also, the diameter of the core 31c with circular cross section is 50 µm when the width of the sample flow 39 is 30 µm.

When the end of core 31c of the optical fiber 31b is circular shape like shown in the cross section diagram in FIG. 12, there is difference between the passage time of the specimen 21 passing through the center of the circle and the passage time of the specimen 21 passing the off-center path. Consequently, since the difference between the specimen 21 flowing paths appears as the difference between the amounts of light received by optical fiber 31b on the light receiving surface of the optical fiber 31b, thereby resulting in the deterioration of the specimen measurement accuracy.

Alternatively, in the case that the core 31c's cross section of the optical fiber 31b is square and is arranged like shown in the cross section diagram in FIG. 13, the passage time of the specimen 21 passing through the center and the passage time of the specimen 21 passing the side in the light receiving area is substantially equal. Therefore, even though the specimen 21 flowing paths are different in the light receiving area, the specimen measurement accuracy is improved since the amount of light received by the optical fiber 31b is substantially equal.

It is preferred that in such square core 31c, the side being in perpendicular direction to the traveling direction of the sample flow 39 is wider than the width of the sample flow 39. This receives the transmitted light, scattered light or fluorescence going out of the sample flow 39 in lateral directions, which leading to high measurement accuracy. As mentioned above, by adjustably arranging multiple optical fibers in traveling direction of the sample flow 39, the measurement accuracy in the sample flow 39 traveling direction is further improved.

In the case that the core 31c's cross section of the optical fiber 31b is square with large width, it is proffered that the length of two sides which is perpendicular in the sample flow 39 traveling direction is two times or more longer than other two sides which is parallel in the traveling direction.

The optical fiber 31 which has square core 31a may be used for light irradiation, or for side scattered light reception described later.

Figure 14:
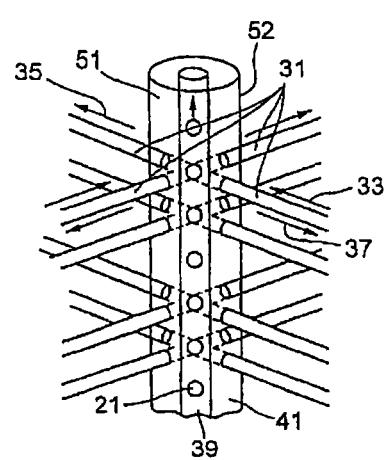
FIG. 14 is a perspective view showing the specimen identifying device related to an embodiment of the present invention.

Next, another specimen identifying device of the present invention is explained with reference to FIG. 14. In FIG. 14, in the circumference of the fine flow path 51 measuring point at one measuring section, two pairs of optical fibers 31, each pair is oppositely arranged, are provided on a same plane. In other word, in one measuring section, four optical fibers 31 circumferentially spaced 90 degree are provided. In FIG. 14, the four measuring section are orderly provided in specimen 21 traveling direction, from the lower of the drawing one by one, in the four-stage structure. The number of the measuring section is not limited to four, which can be determined the installation number according to needs.

Additionally in FIG. 14, in one measuring section, four optical fibers 31 circumferentially spaced 90 degree are provided, but not limited, and the number and installation space can be determined if necessary. In this case, providing two optical fibers 31 oppositely as a pair forms proffered structure since the light irradiation efficiency or light reception efficiency during irradiation or reception is not decreased.

In the structure case above mentioned, identification at one measuring section can be conducted from several directions. As a result, the size and shape of the specimen can be two dimensionally measured, which leading to obtaining more information. Also, providing multiple measuring sections in multiple stages increases the chance of two dimensionally measurement, and identify measuring (observing) in each measuring section with same waveform to identify and measure improves reliability and quantity of information obtained, while the shape of the specimen being measured with better accuracy.

Furthermore, while measuring the transmitted light of the specimen in the above mentioned structure, the backward scattered light specimen may be measured. In this case, two optical fibers 31 are oppositely arranged as a pair as above mentioned. One optical fiber 31 is for transmitting the monitor light and the backward scattered light, and the other optical fiber 31 oppositely arranged is for transmitting the transmitted light. In FIG. 14, two pairs of optical fibers 31, each pair is oppositely arranged, totally four optical fibers 31 are arranged. In FIG. 14, the monitor light is transmitted from two optical fibers, which are at the front side in the drawing, and when the monitor light is irradiated to the specimen, the transmitted light is transmitted to the two optical fibers, which are at the back side in the drawing, while the backward scattered light is transmitted by two optical fibers, which are at the back side in the drawing. As just described, if one specimen is measured the transmitted light and the backward scattered light from two direction, the shape of the specimen can be measured multidirectionally, and more two dimensional information can be obtained. Consequently, the shape of the specimen can be measured with better accuracy.

Figure 15:
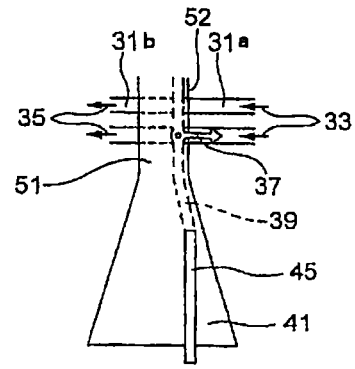
FIG. 15 is a cross sectional-side view showing a deformation example of arrangement of the specimen introduction nozzle in the specimen identifying device related to an embodiment of the present invention.

Next, another specimen identifying method of the present invention is explained with reference to FIG. 15. A specimen identifying device shown in FIG. 15 is characterized by the arranged poison of the specimen introduction nozzle 45. Alternatively, in FIG. 4 and FIG. 14, the specimen introduction nozzle 45 is provided at almost the cross section center of the fine flow path 51. However, the specimen introduction nozzle 45 of the embodiment shown in FIG. 15 is provided at the position where is misaligned from the virtual line connecting the center of the fine flow path 51 and the measuring point. In this manner, by off-center arranging the specimen introduction nozzle 45 enable to permit the sample flow 39 at the place near the detection device of the fluorescence 37. The degree of decentering from the arranged position of the specimen introduction nozzle 45 is determined based on the shape, condition, type of the specimen, flow velocity of the sample flow, and etc. In other word, when more detailed and more accurate specimen identification (observation) is desired, or when the transmissibity of the sheath flow is low, and the like, the nozzle may be arranged such that the sample flow 39 being closer to the detection device of the fluorescence 37.

Additionally, by letting the specimen flow while being closer to the light receiving device side, the peak variation of the amount of light received at the light receiving device of when the specimen passes by can be increased. Therefore, the size, shape and condition of the specimen can be measured with better accuracy.

Figure 16:
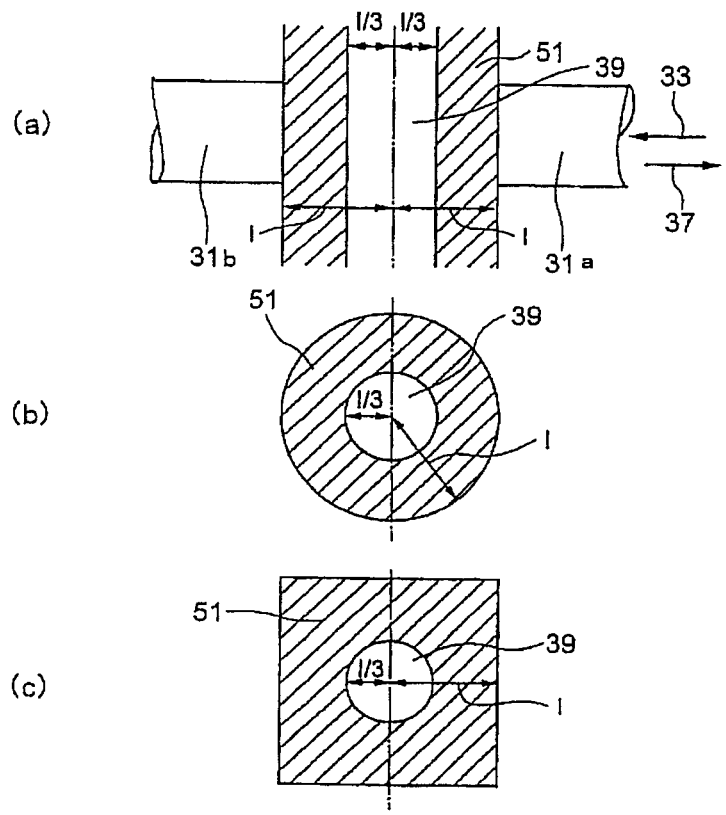
FIG. 16 is a cross sectional-side view and transverse sectional-views showing the region of a specimen supplying path in the specimen identifying device related to an embodiment of the present invention.

Above point is explained with reference to FIG. 16. FIG. 16(a) is the cross section diagram of the identifying device, showing the structure that, by decentering the nozzle arranged position, sample flow 39 is made closer from the center of fine flow path 51 to the light irradiation surface or the light receiving surface. The shaded area illustrated in from 16(a) to (c) is the decentering area. This decentering area is, for example, when the fine flow path is circular, formed as the shaded area of FIG. 16(b), and when square, formed as the shaded area of FIG. 16(c). The position of the optical fiber for irradiating and receiving can be provided at anywhere, in the case that those of optical axis are matched.

Figure 17:
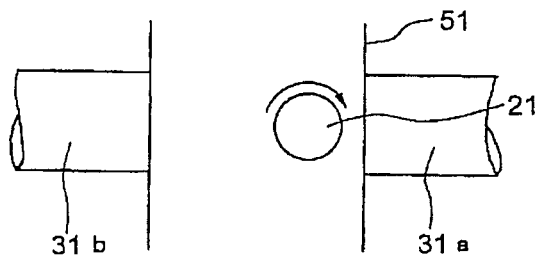
FIG. 17 is a diagram for explaining an operation of the specimen rotation condition in the specimen identifying device related to an embodiment of the present invention.

Next, another specimen identifying method of the present invention is explained with reference to FIG. 17. The present invention is characterized by making the specimen 21 rotate in the sample flow and letting flow into the fine flow path 51, and identifying (observing) this rotating condition in the measuring section.

In this manner, the rotation of the single specimen 21 enables to obtain information on a circumference, for example, although generally the property of the specimen can be obtained only in one direction. Moreover, by increasing the rotation speed of the specimen, information on the circumference can be obtained in a short time. Furthermore, measuring two dimensionally a nonspephirical specimen is possible; thereby more information can be obtained.

Next, a method of rotating specimen is explained. The present invention is characterized by rotating the specimen 21 toward the wall direction where the light irradiation surface and the light receiving surface are provided. For example, in FIG. 17, the specimen is rotating in clockwise direction about the vertical axis shown in the drawing. By keeping this rotation, the circumference of the specimen can be measured.

Figure 18:
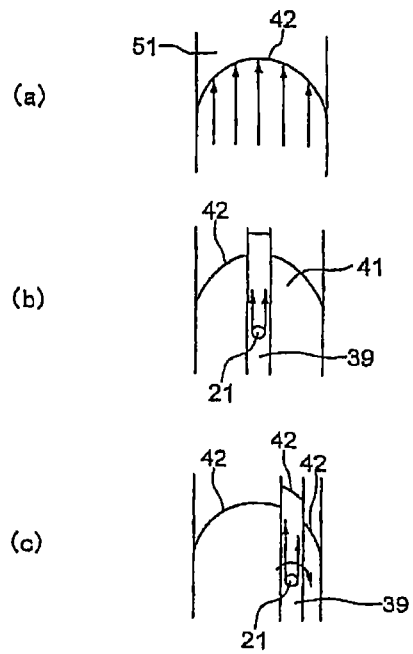
FIG. 18 is a diagram for explaining an operation of the specimen supply system in the specimen identifying device related to an embodiment of the present invention.

This condition is explained with reference to FIG. 18. As shown in FIG. 18(a), the faster velocity gradient 42 of the fine flow path 51 can be seen, the closer to the center of the fine flow path 51 the position is. As shown in FIG. 18(b), In the case of forming the sheath flow 41 and the case of letting specimen 21 flow in the sample flow 39, the speed at right and left of the specimen 21 are same. As shown in FIG. 18(c), in the case of decentering, the difference of the flow velocity indicated by arrows at the right and left of the specimen 21 is generated, which cause the rotary movement to the specimen.

Next, another embodiment of the specimen identifying device of the present invention is explained with reference to FIG. 19 and FIG. 20. This device is specially used for measuring the fluorescence of the specimen.

Figure 19:
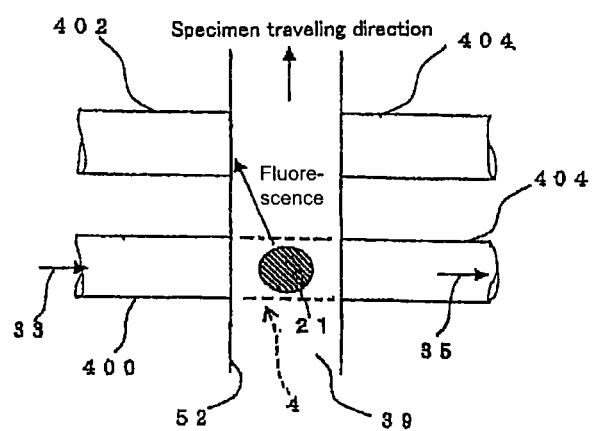
FIG. 19 is a structural diagram of a first example of the relationship between light irradiating position and light receiving position in the specimen identifying device related to an embodiment of the present invention.

A specimen identifying device shown in FIG. 19 receives the fluorescence at other optical fiber 402 than optical fiber 400 for irradiating the monitor light 4. This is for the purpose to perform accurate measurement even if the fluorescence irradiated from the specimen is weak. For example, when the optical fiber 400 for irradiating the monitor light 4 is used for receiving the fluorescence from the specimen, if the monitor light 4 is irradiated to the liquid inside of the flow path for letting the specimen flow or to the internal surface wall of the flow path, the reflected light is generated at the light irradiated section. This reflected light is transmitted with the fluorescence to the light receiving device via optical fiber 400 for irradiating the monitor light 400. That is, at the light receiving device, the light intensity of both reflected light and fluorescence will be measured. Therefore, to perform accurate measurement with, specially, weak fluorescence, not using the optical fiber 400 for irradiating the monitor light 4 but other optical fiber 402, for receiving the fluorescence of the specimen, that enables restraining the reflected light effect of the monitor light 4, which results in improving the light reception sensibility of the fluorescence.

The specimen identifying device shown in FIG. 19 is provided such that the optical fiber 400 for irradiating the monitor light 4 and the optical fiber 404 for receiving the transmitted light 35 or forward scattered light have identical optic axis, and the optical fiber 402 for receiving the fluorescence is provided so as to having the optic axis not aligned with the one of the optical fiber 400. To elaborate, the optical fiber 402 for receiving fluorescence is provided not to align its optic axis with the optical fiber 400 for irradiating the monitor light 400 to the specimen traveling direction (upper side in the drawing).

In this manner, providing optical fiber 400 for irradiating the monitor light 4 and the optical fiber 402 for receiving the fluorescence with being each optic axis off, the time scale of the monitor light 4 irradiation and the fluorescence reception in the measurement can be different. As a result, providing the optical fiber 402 for receiving the fluorescence specially, to align its optic axis from the optical fiber 400 for irradiating the monitor light 400 to the specimen traveling direction makes possible to measure the fluorescence generated by the specimen due to the monitor light 4 irradiation without being affected by the reflection of the monitor light. Especially, high-sensitivity measurement is possible to measure the fluorescence having a long lifetime.

Figure 20:
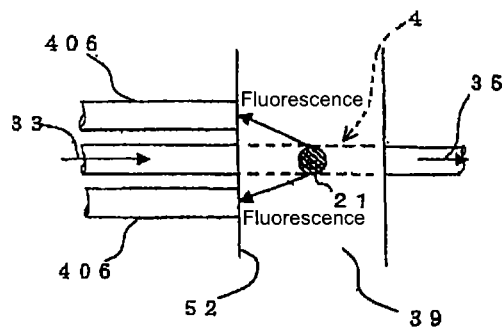
FIG. 20 is a structural diagram of a second example of the relationship between light irradiating position and light receiving position in the specimen identifying device related to an embodiment of the present invention.

In FIG. 19, the optical fiber 402 for receiving the fluorescence is provided to align its optic axis with the optical fiber 400 for irradiating the monitor light 4 to the specimen traveling direction, but as shown in FIG. 20, the second optical fiber 406 for receiving the fluorescence may be provided to align its optic axis with the optical fiber 400 for irradiating the monitor light 400 to the wrong direction of specimen traveling. In other word, in the specimen identifying device shown in FIG. 20, the fluorescence generated from the specimen at the front stage and the back stage in the specimen traveling direction of the optical fiber 400 for irradiating the monitor light 4 will be received. In such structure shown in FIG. 20, in addition to the feature of FIG. 19, since the fluorescence is received by multiple optical fibers, the amount of light received of the fluorescence increases, which leading to the improvement of the sensitivity.

Figure 21:
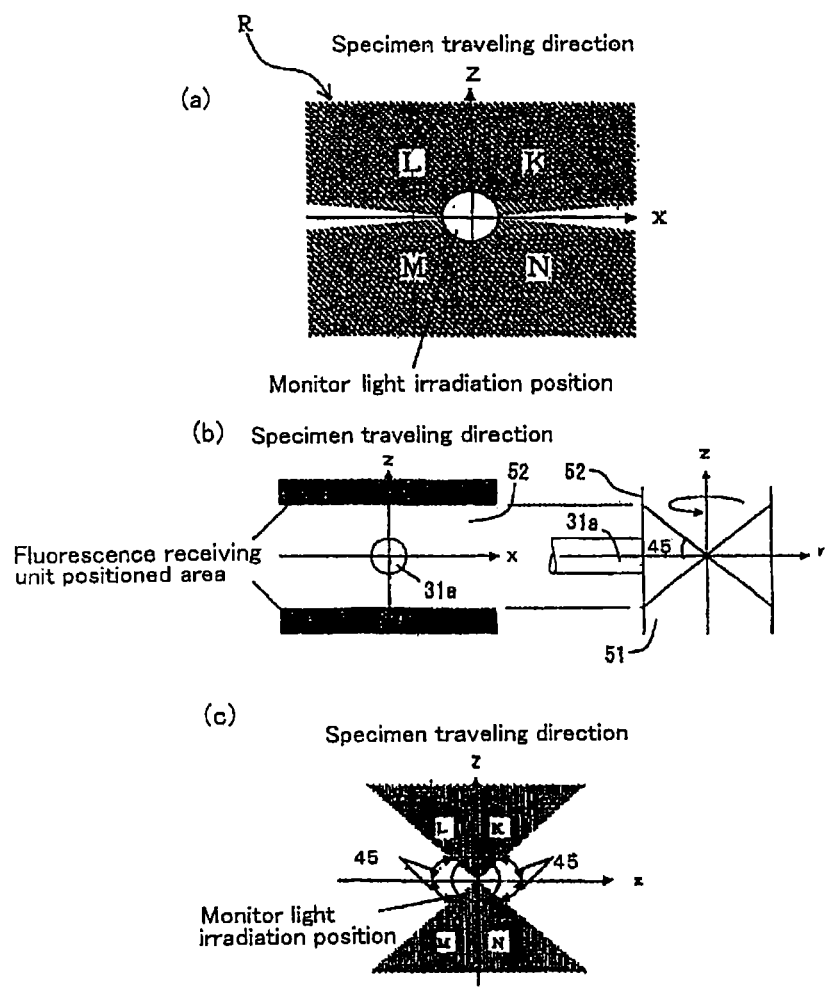
FIG. 21 is a structural diagram of a third example of the relationship between light irradiating position and light receiving position in the specimen identifying device related to an embodiment of the present invention.

Additionally, the installation position of the optical fiber 400 for irradiating the monitor light 4 illustrated in FIG. 19 and FIG. 20 is the area capable of receiving the fluorescence generated from the specimen due to the monitor light 4 irradiation such as diagonal line area R shown in FIG. 21, and at least one or more optical fiber may be provided.

At the diagonal line area R shown in shown in FIG. 21, a necessary number of optical fiber for receiving the fluorescence is provided at a necessary location, but the installation position is characteristically not to be positioned on the X axis which is perpendicular to the specimen traveling direction. This is because, when the fluorescence of the traveling specimen is excited to receive the light, the specimen is just passing or is starting to pass the measuring section at the moment immediately after exciting the specimen, so as to provide the light receiving device to align the position from the identical optic axis plane of the monitor light to the traveling direction as shown in FIG. 21 enables being measured in the light receiving device without being affected by the reflection of the monitor light, which leading to the improvement of the sensitivity.

In other word, to explain with reference to FIG. 21(a), in the case that the specimen travels in the positive direction of the z axis, it is desired to provide the optical fiber for receiving the fluorescence in the K, L area of the diagonal line area R, and in the case that the specimen travels in the negative direction of the z axis, it is desired to provide the optical fiber for receiving the fluorescence in the M, N area of the diagonal line area R. Regarding the light receiving device as shown in FIG. 21(b) and FIG. 21(c), it is desired to be provided at the inner wall of the flow path that is located at a region ±45 degree or more respecting to the specimen traveling direction, while setting the midpoint of the plane flow path which is perpendicular to the specimen traveling direction including the optic axis of the light receiving device as the center, specially in the diagonal line area R.

Figure 22:
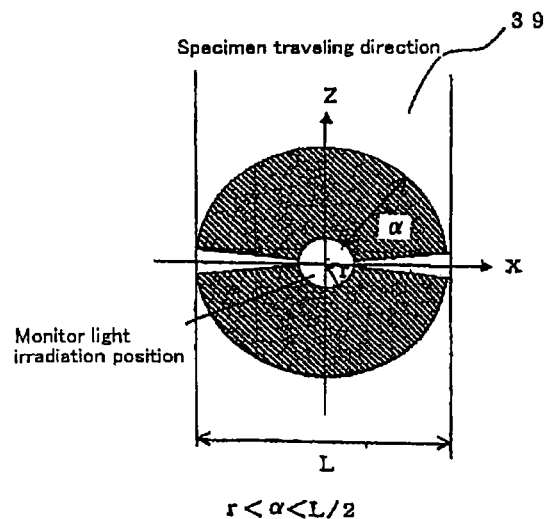
FIG. 22 is a structural diagram of a fourth example of the relationship between light irradiating position and light receiving position in the specimen identifying device related to an embodiment of the present invention.

Providing the optical fiber 31b for receiving the light at the area shown in FIG. 21(a) to (c) is capable of measuring with better sensitivity, and a more proffered relation of the installing position with the optical fiber for irradiating the monitor light 4 is shown in FIG. 22. In FIG. 22, when setting the width of the sample flow 39 is L, the radius of the monitor light irradiation section is r, fluorescence the radius of the light receiving device are is α, the center of the fluorescence light receiving device is set within the are that has the radius α of r<α<L/2, while placing the monitor light irradiation section as the center, is desired.

In the embodiment in FIG. 19, FIG. 20 and FIG. 21(a), (b), (c) above mentioned, only one optical fiber for irradiating the light is provided and at least one or more optical fiber for receiving the light is provided, and vice versa may be formed. That means, providing multiple optical fibers for irradiating the light and only one optical fiber for receiving the fluorescence is also possible. In the case of providing multiple optical fibers, using a bundle fiber or optical connector, or such facilitates the positioning, etc. in installation.

Figure 23:
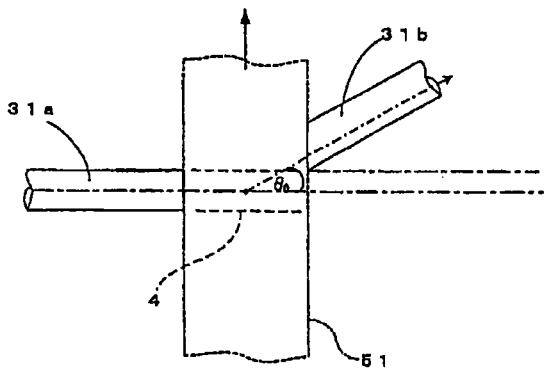
FIG. 23 is a structural diagram of a fifth example of the relationship between light irradiating position and light receiving position in the specimen identifying device related to an embodiment of the present invention.
Figure 24:
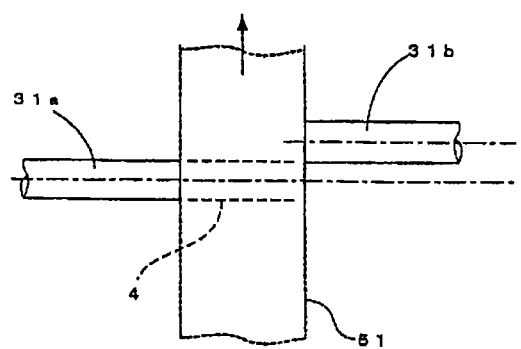
FIG. 24 is a structural diagram of a sixth example of the relationship between light irradiating position and light receiving position in the specimen identifying device related to an embodiment of the present invention.
Figure 25:
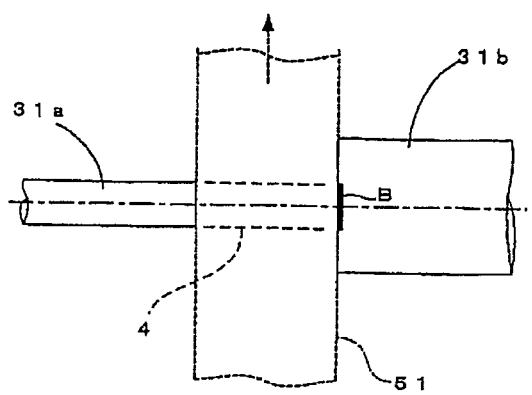
FIG. 25 is a structural diagram of an example of the relationship between light irradiating position and light receiving position in the specimen identifying device related to an embodiment of the present invention.

As shown in FIG. 23, in the case that a control point is set as the cross point of the optic axis of optical fiber 31a for irradiating the light and the central axis of the fine flow path 51, it is proffered to arrange the optical fiber for receiving the fluorescence or the scattered light, with respect to the optic axis of optical fiber 31a for irradiating the light, the light receiving surface is present in the direction of angle θ in the fine flow path 51 traveling direction from the control point. The angle θ is, for example, 8 degree under the condition that the fine flow path 51 has a diameter of 0.1 mm and the optical fibers 31a, 31b have core diameters of 50 to 100 μm. Or, as the angle θ, it is desired to select an angle that keep the optic axis of the optical fiber 31b for receiving the light, 100 μm or the like away from the center of the light receiving surface of the optical fiber 31a for irradiating the light. In this manner, diagonally arranging the optical fiber 31b for receiving the light with respect to the light traveling direction improves the light reception efficiency. To prevent the optical fiber 31b protruding into the fine flow path 51, it is proffered to cut the front end of the optical fiber 31 diagonally. Additionally, as shown in FIG. 24, the light receiving surface of the optical fiber 31b for receiving the light can be located at the area where is out of the light irradiation region where the light from the optical fiber 31a for irradiating the light comes directly. Or, as shown in FIG. 5, at least one part of the area from the optical fiber 31b for receiving the light of light irradiation region where the light from the optical fiber 31a for irradiating the light comes directly may be covered with a light shielding member B.

For example, in the case that the core diameter of the optical fiber 31a for irradiating the light is 50 μm and the core diameter of the optical fiber 31b for receiving the light is 100 μm, the center of the core of the optical fiber 31b for receiving the light is covered by the light shielding member B that has a diameter of 50 μm. The light shielding member B is such as metal film and multilayer structured dielectric film.

In any case, by providing the light receiving surface of the optical fiber 31b at a location where the direct light coming from the optical fiber 31a for irradiating the light and the scattered light or the fluorescence don't cross, the light reception efficiency of the scattered light or the fluorescence is improved.

Next, an arrangement of the optical fiber for receiving the side scattered light generated from the specimen 21 is explained.

Figure 26:
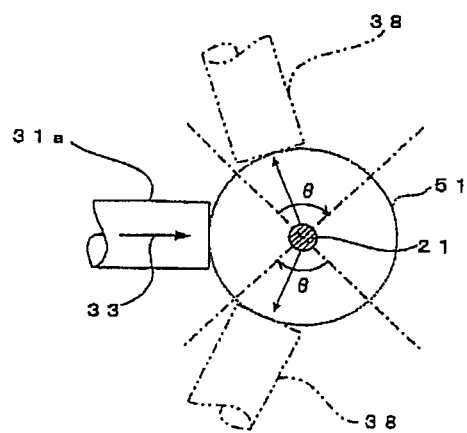
FIG. 26 is a perspective view of an example of the specimen identifying device related to an embodiment of the present invention.

The location of the optical fiber for receiving the side scattered light needs to prevent being mixed with the forward scattered light. FIG. 26 shows the location of the optical fiber for receiving the side scattered light. In the FIG. 26, the traveling direction of the fine flow path 51 is perpendicular direction to the paper surface.

On the extended line of the optic axis of the optical fiber 31a for irradiating the light shown in FIG. 26, while setting the cross point of the central axis of the fine flow path 51 and the optic axis of the optical fiber 31a as the origin point, the light receiving surface of the optical fiber 38 for receiving the side scattered light is located within the range of 45 to 135 degree and 2245 to 315 degree to the light traveling direction. Thereby, the side scattered light is received by the optical fiber 38 for receiving the light 8 efficiently.

Figure 27:
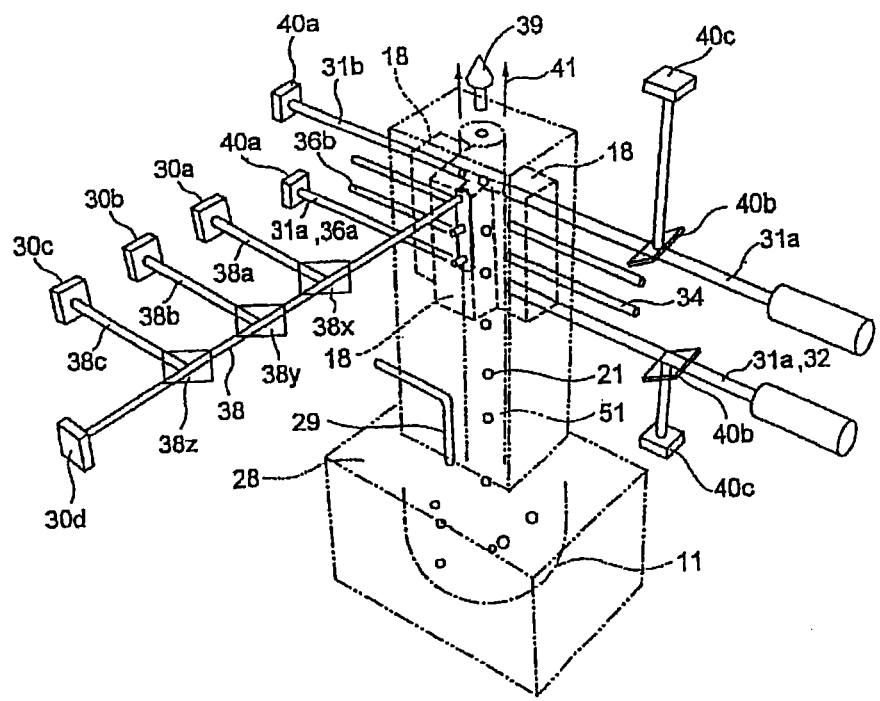
FIG. 27 is a diagram for explaining the specimen identification related to an embodiment of the present invention.

As explained in above, the arrangement of optical fiber 31a for irradiating the light to the specimen 21, optical fiber 31b for receiving transmitted light through the specimen 2, the optical fiber 34 for receiving the fluorescence of the specimen 21 and the optical fiber 38 for receiving the side scattered light is shown in FIG. 27. Additionally, in FIG. 27, numeral 38a, 38b, 38c indicate the optical fiber for dispersing which is branched into the optical fiber 38 for receiving the side scattered light via dichotic mirrors 38x, 38y, 38z, and numeral 30a to 30d indicate photomultipliers (PMT) which is connected to the end of the optical fibers 38, 38a, 38b, 38c for receiving the side scattered light. The dichotic mirrors 38x, 38y, 38z, disperse, such as FITC (fluoresce in isothio-cyanate), GFP (green fluorescent protein), PI (propidium iodide), PE (R-phycoerythrin), fluorescence analyzing PerCP in order of far position from the fine flow path 51. Furthermore, numeral 40a indicates a photodiode for receiving the light passing through the optical fiber 31b for transmitted light, numeral 40b indicates a nonreciprocal optical device for selectively dispersing the backward scattered light passing thorough the optical fibers 31a, 32 for irradiating the light, and numeral 40c indicates a photodiode for receiving the dispersed backward scattered light by the nonreciprocal optical device 40.

Next, a monitor light irradiating method to the specimen and a monitor light irradiation condition to the specimen are explained with reference to FIG. 4, FIG. 14, and FIG. 15. As shown in FIG. 4, FIG. 14, FIG. 15, the front end of the optical fiber for irradiating the monitor light 33 is installed at the inner surface of the wall 52 without providing with a light concentrating means. In other word, the monitor light 33, as shown in FIG. 4, FIG. 14, FIG. 15, is not concentrated at the front end of the optical fiber, and is irradiated to the specimen in non concentrated state.

In this manner, when the monitor light irradiated to the specimen is not in concentrated state, even if the specimen passes through any position of the flow path, distribution deviation of the irradiated monitor light energy is less. Alternately, if a condensed monitor light is irradiated to the specimen, since the measurement is performed by passing the specimen to the condensing location, in the case where the location of specimen flow deviates from the condensed center position, the energy distribution deviation of the monitor light to the specimen increases. So that, for example variation of the transmitted light measurement increases, which deteriorates the measurement accuracy.

At the same time, in this embodiment, since the light irradiated from the optical fiber is directly irradiated to the fine flow path 51 without any process, the shielding variation of the monitor light due to specimen is not much even if the specimen passes any position as well as center in the sample flow path 39, so that the measurement accuracy is improved.

(Specimen Delivery Device)

Figure 28:
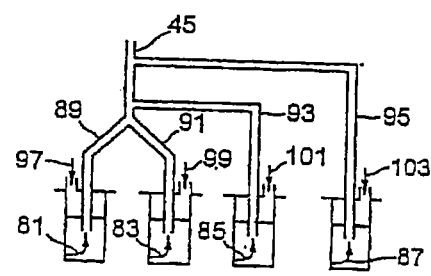
FIG. 28 is a structural diagram of a first example of a delivery device for a specimen identifying sample related to an embodiment of the present invention.

Next a delivery device installed at the front stage of the specimen identifying device of the present invention is explained with reference to FIG. 28. This delivery device may be installed if necessary. The lower end of the specimen introduction nozzle 45 is branched into a plurality of sample supplying nozzle 89, 91, 93, 95, which forms a structure capable of sucking a plurality of samples 81, 83, 85, 87. More specifically, the plurality of samples supplying nozzles 89, 91, 93, 95 have the structure capable of merging into the specimen introduction nozzle 45 at the end of the downstream thereof conclusively. By forming such structure in FIG. 28, controlling pressures 97, 99, 101, 103 without operating the specimen identifying device can achieve introduce of the plurality of samples 81, 83, 85, 87.

For example, when the sample 81 is measured, the pressure 97 is needed to be higher than pressure 99, 101, 103, at that time the pressures 99, 101, 103, is controlled to prevent the sample 81 running backwardly into the samples 83, 85, 87.

Moreover, while the flow path being prefilled with liquid, by letting the minute amount of samples 81, 83, 85, 87 flew by controlling the pressures 97, 99, 101, 103, in pulse condition, very minute amount of sample such as several nl (nano liter) can be measured.

Figure 29:
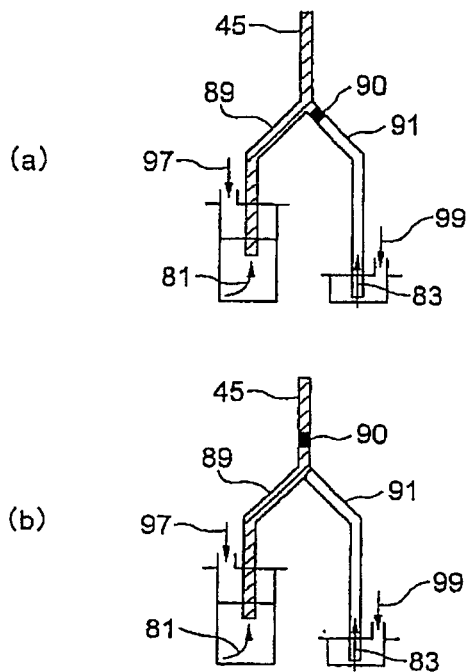
FIG. 29 is a structural diagram of a second example of a delivery device for a specimen identifying sample related to an embodiment of the present invention.

The above method for letting the minute amount of sample flow in pulse condition is explained with reference to FIG. 29. First, the pressure 97 is set higher than the pressure 99, and the flow path 89 and the specimen introduction nozzle 45 is filled with the dummy sample 81. The pressure 99 is set such that the dummy sample 81 does not go into the flow path 89, nor minute amount of sample 90 go into flow path 89. Therefore, the dummy sample 81 and the minute amount of sample 91 have balance shown in FIG. 29 (a). And then, setting the pressure 97 to be lower than the pressure 99 momentaneously introduces the minute amount of sample 90 into the specimen introduction nozzle 45. Further, in the next moment, setting the pressure 97 to be higher than pressure 99 introduces the minute amount of sample 90 into the specimen introduction nozzle 45, in the condition that the minute amount of sample 90 is being sandwiched by the dummy sample 81. Thereby the minute amount of sample 90 is formed in the specimen introduction nozzle 45 as shown in FIG. 29 (b). Accordingly, the specimen introduced in pulse condition can be minute amount. Also, a valve for switching the channel and a regulator for pressurizing may is used.

Figure 30:
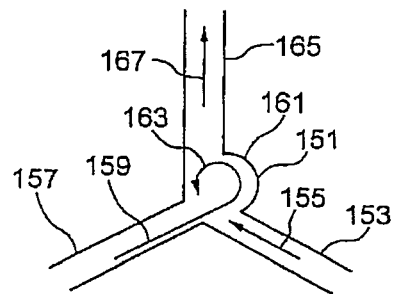
FIG. 30 is a structural diagram of a third example of a delivery device for a specimen identifying sample related to an embodiment of the present invention.
Figure 31:
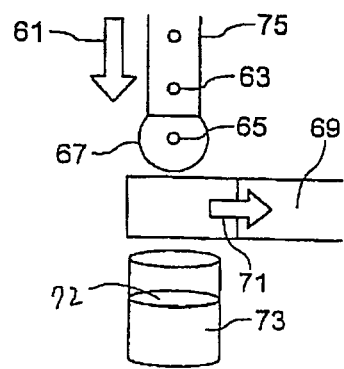
FIG. 31 is a structural diagram of a first example of the specimen dispensing device related to an embodiment of the present invention.
Figure 32:
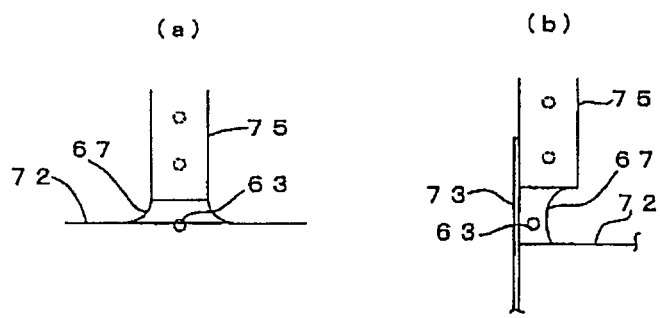
FIG. 32 is a structural diagram of a second example of the specimen dispensing device related to an embodiment of the present invention.
Figure 33:
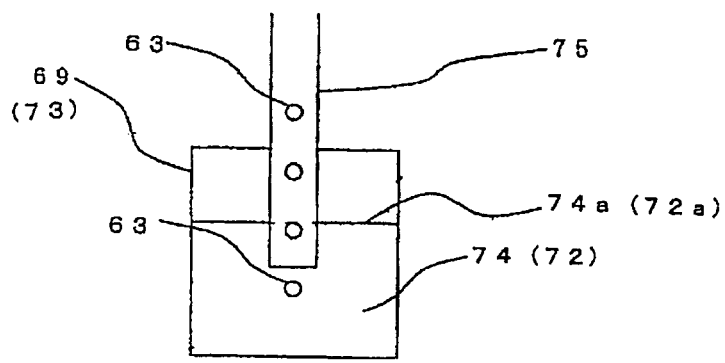
FIG. 33 is a structural diagram of a third example of the specimen dispensing method related to an embodiment of the present invention.
Figure 34:
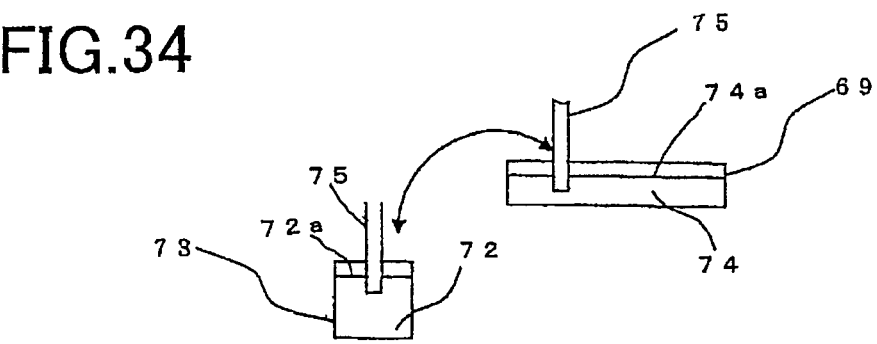
FIG. 34 is a structural diagram of a fourth example of the specimen dispensing device related to an embodiment of the present invention.
Figure 35:
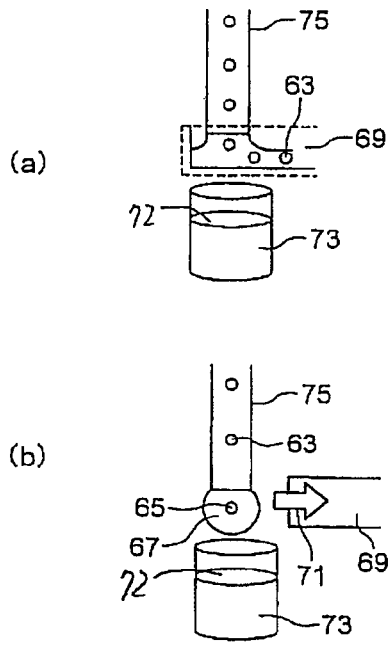
FIG. 35 is a structural diagram of a fifth example of the specimen dispensing device related to an embodiment of the present invention.
Figure 36:
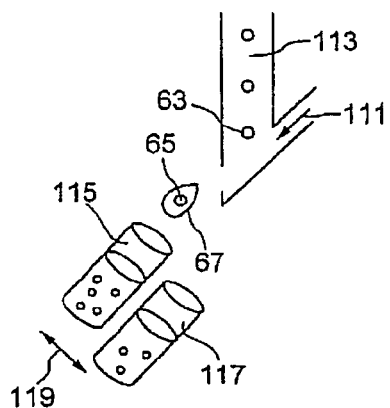
FIG. 36 is a structural diagram of a sixth example of the specimen dispensing device related to an embodiment of the present invention.

Next, another embodiment of the delivery device of the present invention is explained with reference to FIG. 30. In the case a liquid for suspending the specimen by use of the branch nozzle shown in FIG. 28 is mixed with such as a liquid for transporting the specimen or a liquid for suspending the specimen, merging liquids often forms laminar flow of liquids. To mix such laminar flow state liquid, it is necessary to generate a turbulent flow at the merging point. Accordingly, a concaved portion or convex portion is provided near the merging point. In other word, this is an example of a concaved portion 161 provided so as to generate a turbulent flow 163 when a liquid for suspending the specimen 155 sucked with one of branch nozzle 153 and a liquid for suspending the specimen 159 sucked with one of branch nozzle 157 are merged at a merging point 151.

(Specimen Dispensing)

Next, a specimen dispensing device of the present invention is explained. The dispensing is a process for calculating a time taken until the specimen is discharged based on a flow velocity of the specimen that is measured at the measuring section of the specimen identifying device, collecting only necessary specimen and disposing of unnecessary specimen.

The specimen dispensing device of the present invention is explained with reference to FIG. 31. For example, by pressurizing 47 of the sheath flow 41 pressure and a sample transfer pressure shown in FIG. 4, liquid droplets 67 or a liquid flow containing a target specimen 65 is formed on the front end of a dispensing nozzle 75. This liquid droplets 67 or liquid flow may contain a non-target specimen 63 identified with the presence or the level of the identifier.

This liquid droplets 67 or liquid flow, in case of containing the non-target specimen 63, is free fell to a drain tank 69 and discharged, but in case of containing the target specimen 65, the drain tank 69 moves in a sliding direction 71 and the target specimen 65 can be dispensed by inserting a dispensing nozzle 75 into a nozzle container 73 filled with a liquid by delivery means 61. The use of this specimen dispensing device enables to dispense without applying extra stress to the specimen, without forming liquid droplets by using a conventional method such as ultra sonic or high electric pressure, so that a high survival rate after dispensing of living cells is expected for example.

The specimen is protected and stored in the liquid or liquid droplets until the completion of dispensing.

Besides, another method for collecting the target specimen 65 and discharging the non-target specimen are explained with reference to FIG. 32, FIG. 33 and FIG. 34. First, when the dispensing nozzle 75 is in normal state, to make a condition that the liquid flow running from the dispensing nozzle 75 flows continuously in directly contact with the liquid surface of the drain tank 69 (in the liquid shown in FIG. 34) without pause, a relative position between the dispensing nozzle 75 and the drain tank 69 is adjusted. In this case, an attention should be paid not to the liquid droplets 67 are separated from the front end of the dispensing nozzle 75 nor surrounded whole of it by air (gas) until it is contained by the solution 72 in the container 73. For example, the liquid droplets 67 are controlled by the nozzle moving means 61 so as to move the liquid droplets 67 containing the target specimen 65 from the nozzle moving means 61 to the solution 72, like shown in FIG. 32(*a*), (*b*), before falling down from the dispensing nozzle 75.

Then, when in a dispensing state where the target specimen to be dispensed is sensed, relative position between dispensing nozzle and drain tank 69 is changed as shown in FIG. 34, and the relative position between the dispensing nozzle 75 and the collection container 73 is changed such that the liquid flow or the liquid droplets containing the target specimen is dispensed to the collection container 73 after the liquid flow or the liquid droplets flowing from the dispensing nozzle 75 is separated from the liquid in the drain tank 69. After the target specimen is dispensed to the collection container 73, the dispensing nozzle 75 is returned to the before-mentioned normal position. When above mentioned dispensing, it is prefer that the liquid discharging or dispensing is conducted while the front end of the dispensing nozzle being positioned at the liquid surface level or lower in the liquid of the drain tank 69 and the collection container 73. In this manner, by controlling the front end location of the dispensing nozzle, the dispensing can be carried out without waiting a complete liquid droplets formation, so that it is possible to dispense very speedy without applying stress to the specimen (cell), without forming liquid droplets by using a conventional method such as ultra sonic or high electric pressure.

Furthermore when adjusting the relative position among the dispensing nozzle 75, the drain tank 69 and the collection container 73, it is proffered that at least one front end of the dispensing nozzle 75 is moved in curve linear motion with centering an arbitrary point between drain tank 69 and collection container 73 as shown in FIG. 34. In this way, by moving the dispensing nozzle 75 in curve linear motion, only one axis is activated in dispensing that enables high speed dispensing, and a single cell is dispensed within one second.

In the above mentioned dispensing, the front end of the dispensing nozzle may be contacted the liquid level or in the liquid of the drain tank 69 and the collection container 73 as explained in FIG. 33, or may not, which is selected properly.

Next, another specimen dispensing device of the present invention is explained with reference to FIG. 35. When a non-target specimen 63 is passes, the front end of the nozzle 75 is inserted into the drain tank 69 to discharge, the drain tank 69 is evacuated to the sliding direction 71 on the timing of target specimen 65 flow, and the front end of the nozzle 75 is inserted into the collection container 73 to eject (dispense) the specimen. By use of the specimen dispensing device, comparing to the method using the dispensing device shown in FIG. 31, since the specimen is dispensed without waiting the liquid droplets falling by its weight, the speedy dispensing is enabled. Also, the dispensing is carried out without applying extra stress.

Next, a further specimen dispensing device of the present invention is explained with reference to FIG. 36. By forming the liquid droplets 67 by constant application of an air pressure 111 from the front end side section of a nozzle 113 to drive containers 115, 117, the target specimen 65 and the non-target specimen 63 are dispensed. Two or more containers may be provided. Using this dispensing device enables faster dispensing as same as FIG. 35. In order to make this dispensing speed much faster, increasing the speed of driving 119 of the container 115, 117 is effective. Additionally, this gives an effect capable of dispensing without applying extra stress.

Next, yet other specimen dispensing device of the present invention is explained with reference to FIG. 37. By hitting a member 121 provided at the front end of the nozzle 75 with a member 123, a predetermined vibration is generated to form the liquid droplets 67, and by driving 119 the containers 115, 117, the target specimen and the non-target specimen are dispended. In order to make this dispensing speed much faster, increasing the speed of driving 119 of the container 115, 117 is effective. Additionally, this gives an effect capable of dispensing without applying extra stress. Also, by use of this dispensing device, the dispensing can be carried out without applying extra stress similarly to FIG. 31, FIG. 35 and FIG. 36.

Figure 37:
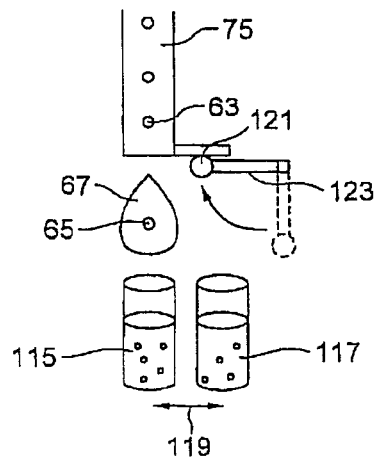
FIG. 37 is a structural diagram of a seventh example of the specimen dispensing device related to an embodiment of the present invention.
Figure 38:
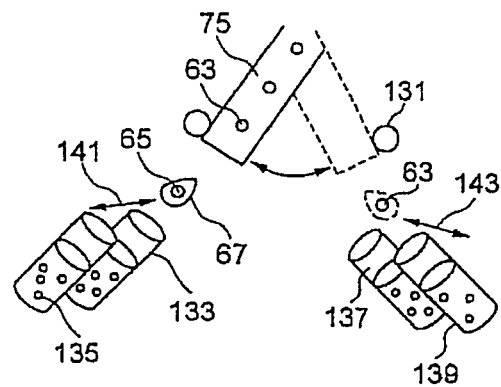
FIG. 38 is a structural diagram of an eighth example of the specimen dispensing device related to an embodiment of the present invention.

Next, further specimen dispensing device of the present invention is explained with reference to FIG. 38. By shaking the nozzle 75 to crush it against a member 131, the liquid droplets 67 is formed by the vibration, and by driving 141, 143, containers 133, 135, 137, 139, the target specimen 65 and the non-target specimen 63 are dispended. Four or more container may be provided. By use of the specimen dispensing device, comparing to the method using the dispensing device shown in FIG. 37, the double speed dispensing is enabled. In order to make this dispensing speed much faster, increasing the speed of driving 141, 143 of the containers 133 to 139 is effective. Also, by use of this dispensing device, the dispensing can be carried out without applying extra stress similarly to the device shown in FIG. 31, FIG. 35, FIG. 36 and FIG. 37.

In addition, in case of using the specimen dispensing device in FIG. 31, FIG. 35, FIG. 36, FIG. 37 and FIG. 38, the dispensing can be carried out based on the shape, size or condition even though the specimen is not fluorescence labeled.

This is because, in the above mentioned specimen identifying device, the shape, size or condition of the specimen that is not be fluorescence labeled can be measured. In other word, by feed forwarding the shape, size or condition of the specimen in the specimen identifying device and the flow velocity of the specimen to control the dispensing device, the specimen can be dispensed according to needs.

Figure 39:
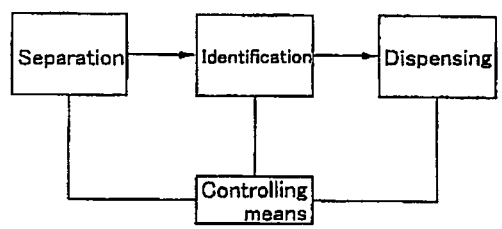
FIG. 39 is a block diagram of a separating, identifying, dispensing and controlling means related to an embodiment of the present invention.

According to an analyzing device that is combined with the above mentioned specimen separating device, the specimen identifying device, and the specimen dispensing device, in the case where a single cell is collected from a cell aggregation of a cell stem, for example, as shown in FIG. 39, by passing the specimen through in order of the specimen separating device, the specimen identifying device, and the specimen dispensing device, separation, identification, dispense can be carried out. Consequently, the single cell can be collected from the cell aggregation without damaging the specimen. In this case, by interlockingly controlling the specimen separating device, the specimen identifying device and the specimen dispensing device, the process of collecting the single cell from the cell aggregation is automatically conducted. In other word, by inputting operation environments of each device into the controlling means and letting the controlling means input the operation environment to each device, a series of the process of the separation, identification, dispense is automatically carried out.

Furthermore a sterilization method for each device of the above mentioned separation, identification, dispensing and a combined device is explained. At the beginning, the sterilization method before measurement is explained.

One way of the sterilization method is a method for irradiating UV (ultraviolet) on each device. This utilizes a sterilization effect of UV by irradiating UV (ultraviolet) on each device. At that time, there is a possibility that there may be some parts where cannot be subjected UV irradiation dispending on a structure of each device. In this case, sterilization can be performed by spraying alcohol to the parts where cannot be sterilized by UV irradiation.

Also, as another way of the sterilization method, it may constitute a structure where each device or whole device of the combination of each device is stored in a chamber, a filter is provided with an air hole, and ventilation is performed if necessary. In other word, the structure where each device or whole device of the combination of each device is stored in a compact clean room. In this case, by providing an air ventilation device having photo catalyst at the air hole and sending sterilized air, a measuring environment with better sterilization can be obtained.

As father way of the sterilization method, the chamber storing each device or whole device of the combination of each device may be filled with sterilizing gas such as ethylene oxide. By sterilizing with gas, small members or parts of each device can be sterilized. In this case, each device can be sterilized by filling a chamber with sterilizing gas such as ozone generated by a UV lamp provided in the chamber.

Sterilizing a flow path through where the specimen flows in each device is the most important, and the sterilizing method of the flow path is explained as below. First, regarding the sterilizing method before measurement, approx. 70% concentration of ethanol may be permitted flow the flow path. The amount of flow, the flow velocity, the number of flow time can be determined according to the level of flow path contamination. Next, regarding the sterilizing method after measurement, concentration of approx. 70% ethanol, and then may be permit flow the flow path. In the sterilizing method after measurement, similar to the sterilizing method before measurement, the amount of flow, the flow velocity, the number of flow time can be determined according to the level of the flow path contamination. Besides, filling a gas having the above mentioned sterilizing effect with the flow path can perform the sterilization.

Figure 40:
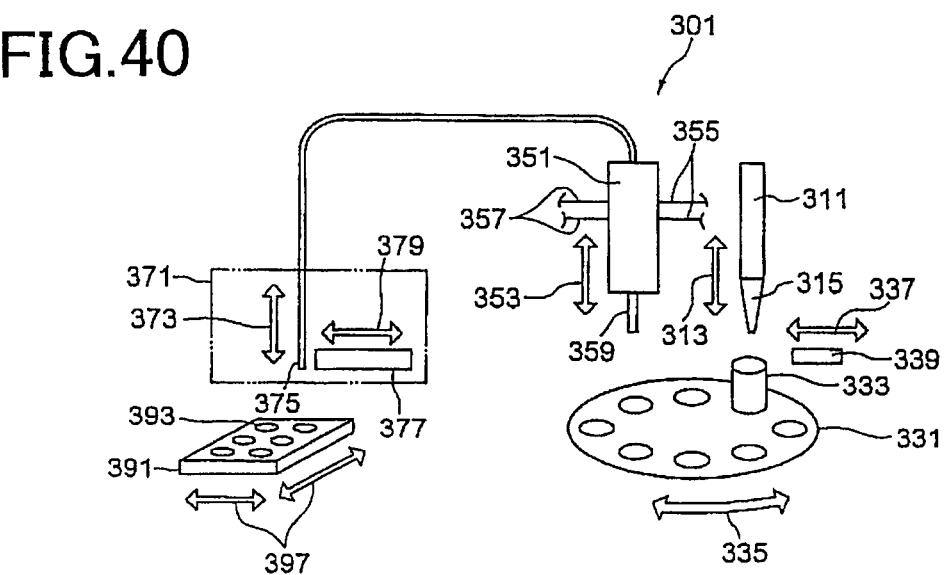
FIG. 40 is a structural diagram of an analyzing device related to an embodiment of the present invention.
Figure 41:
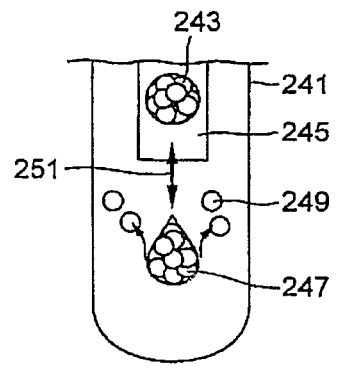
FIG. 41 is an example of stirring in prior art.
Figure 42:
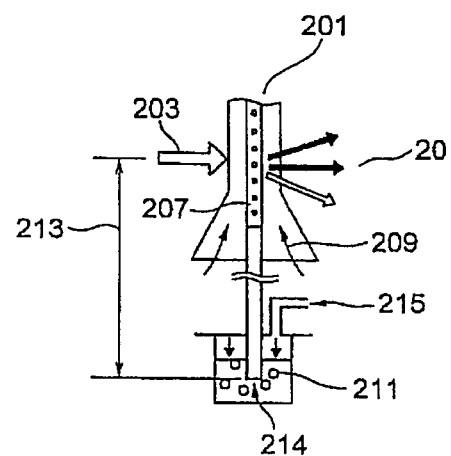
FIG. 42 is an example of specimen identifying in prior art.
Figure 43:
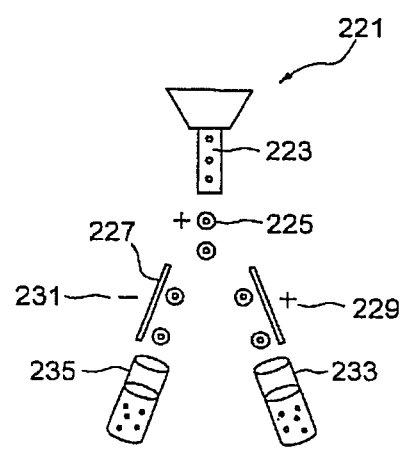
FIG. 43 is an example of specimen dispensing in prior art.

Next, an analyzing device related to an embodiment of the present invention is explained with reference to FIG. 40. An analyzing device 301 for conducting separation, identification, dispense relating to the present invention mainly comprises, a separating device 311 for separating a condensed state specimen, an identifying device 351 for identifying the specimen delved from the separating device 311, and a dispensing device 371 for dispensing a target specimen into a container 391.

The separating device 311 is composed of a nozzle 315 for sucking/ejecting the specimen, a suction/ejection force controlling means for controlling an ejection force of eject the specimen sucked in the nozzle to outside of the nozzle, a nozzle operating means for moving nozzle vertically and laterally, and optical fibers oppositely provided on a wall according to needs, and so on. For the separating device 311, the above mentioned device for separating the specimen is used.

Furthermore the identifying device 351 comprises a flow path thorough where a sacked sample liquid and a sheath liquid sample flow passes by, and a pair of optical fibers which is oppositely located with sandwiching the sample flow. For the identifying device 351, the above mentioned device for identifying the specimen is used.

Furthermore, the dispensing device 371 comprises a dispensing nozzle 375, a nozzle moving means 373 for moving the dispensing nozzle up and down, a drain tank 377 for receiving a non-target specimen, a sliding means 379 for sliding the drain tank 377, and so on. For dispensing device 371, the above mentioned device for dispensing the specimen is used.

The analyzing device 301 having such structure is operated by steps as followings:

(1) First a container 333 containing a condensed specimen is set on a rotating base 331. At that time, a liquid quantity of the sample in the container 333 is about 500 μl.

(2) The rotating base 331 which is rotatable provided is rotated by a rotating means 335 to move a position of the container 333 to be aligned with a position of the nozzle 315 in the separating device 311.

(3) The separating device 311 is moved by the nozzle operating means 313 to move a front end of the nozzle 315 to the height such as 3 mm from the bottom surface of the container 333.

(4) By use of the separating device 311, about 150 μl (micro liter) of the sample liquid quantity in the container 333 is reputedly sucked and ejected by the nozzle 315 for several to several dozens of times with the nozzle controlling means 313 to separate the condensed specimen.

(5) The size of the specimen is measured by an identifying device connected with the separating device 311, which is not illustrated, or by an identifying device 351 connected with the separating device 311.

(6) A 100 μl of the solution containing the separated specimen is sucked by the nozzle 315 in the separating device 311.

(7) Then, by using a filter 339, which is movably provided by such as moving means 337, made of metal and the like having a diameter of 100 μm and the like, the solution is filtered and the insufficiently separated specimen is eliminated.

(8) The solution containing the specimen filtered through the filter 339 is injected into another container 334 by the rotation of the rotating base 331.

(9) The solution containing the filtered specimen is added a diluted solution. The diluted amount is adjusted such that the specimen amount is 1 μl per piece.

(10) The solution containing the filtered specimen is stirred by suction/ejection using the separating device 311 such that the specimen is uniformly dispersed in the solution.

(11) The container 334 with the solution containing the diluted specimen is delivered to a position below the identifying device 351 by rotating with the rotating base 331 and the rotating means 335.

(12) By lowering the identifying device 351 with a moving means 353, a suction nozzle 359 provided at the front end of the identifying device 351 is inserted into the container 334.

(13) An open upper end of the container 334 is sealed with a lower end of the identifying device 351 and a upper end of the container, and then a pressure air is applied to inside of the container 334 to introduce the solution containing the specimen into the identifying device 351. In this case, the flow amount of the solution is for example 0.7 μl/s and the flow velocity is for example 1 m/s. At the same time, the sheath liquid is introduced into the flow path in the identifying device 351 from another hole provided in the identifying device 351.

The shape of the suction nozzle 359 having an inner diameter of 0.3 mm and a length of 35 mm, and the grain diameter of the sample flow 39 through where the specimen flows is 0.03 mm. A distance 43 from a suction/ejection opening of the nozzle to the measuring section is about 50 mm, and the capacity to the measuring section was 2.5 μl as a result.

The diameter of the sheath flow at the measuring section is for example 0.1 mm.

(14) The specimen is delivered to the identifying device 351 while forming the sheath flow. In this case, the sample flow is narrowed down or widen according to the shape of the specimen to make a diameter where the specimen passes by the measuring point one by one (around 10 to 100 mm). Each specimen passes by the measuring points spaced by 100 μm per several seconds.

(15) The specimen is measured at a measuring point having a light irradiation optical fiber 355 and a light receiving optical fiber 357 provided with the side of the sheath flow in the identifying device 351. Here, the presence and the intensity of the fluorescence, the shape of the specimen, and so on are measured. The measuring points are provided in a multiple stage, and the flow velocity of the specimen is measured at these multistage measuring points.

(16) When collecting only fluorescence irradiation specimen is desired, first, from the flow velocity of the fluorescence irradiation specimen measured at the measuring point and the distance from the measuring point to the font end of the dispensing nozzle 375 in the dispensing device 371, an arrival time to the front end of the dispensing nozzle 375 is calculated. The inner diameter of the dispensing nozzle 375 is for example 1 mm.

(17) Then, the dispensing is carried out while matching the timing of the specimen arrival to the front end of the dispensing nozzle 375.

(18) At the front end of the dispensing nozzle 375, liquid droplets including the target specimen is formed. The non-target specimen is let free fall to a drain container 377. When the target specimen arrives, the drain tank 377 is moved by the sliding means 379. And then, by the nozzle moving means 373, the dispensing nozzle 375 is inserted into a well 393 in a container 391 to dispense.

(19) To the well 393 in the container 391, from one to arbitrary number of cells are dispensed. Besides, to another well 393, the dispensing is carried out by moving the container 391 backwardly, forwardly, laterally, vertically and so on with a moving means 397.

FIELD OF INDUSTRIAL APPLICATION

It is usable to measure a specimen for regeneration medicine and cell study, etc.

What is claimed is:

1. A specimen sorter, comprising:
   a separating device to remove a specimen from a container;
   a detection device to identify the specimen as a target specimen or a non-target specimen; and
   a dispensing device to dispense the specimen, the dispensing device comprising:
      a dispensing nozzle and a vibration member, wherein one of the dispensing nozzle and the vibration member moves relative to the other of the vibration member and the dispensing nozzle from a position in which the dispensing nozzle is not in contact with the vibration member to a position in which the dispensing nozzle and the vibration member collide to form liquid droplets at a front end of the dispensing nozzle and to dispense the liquid droplets;
      a first container to collect the liquid droplets dispensed from the dispensing nozzle that contain the target specimen; and
      a second container to collect the liquid droplets dispensed from the dispensing nozzle that contain the non-target specimen.

2. The specimen sorter according to claim 1, wherein the dispensing device further comprises:
   a driving device to move the first container and the second container to collect the liquid droplets.

3. The specimen sorter according to claim 1, wherein the dispensing device further comprises:
   a third container to collect the liquid droplets dispensed from the dispensing nozzle that contain the target specimen; and
   a fourth container to collect the liquid droplets dispensed from the dispensing nozzle that contain the non-target specimen.

4. The specimen sorter according to claim 3, wherein the dispensing device further comprises:

a driving device to move the first container, the second container, the third container, and the fourth container to collect the liquid droplets.

5. The specimen sorter according to claim 1, wherein the liquid droplets in the dispensing nozzle are formed by a predetermined vibration generated when the dispensing nozzle and the vibration member collide.

6. The specimen sorter according to claim 1, wherein the nozzle includes a front end member at the front end of the nozzle, and the vibration member is moved to collide with the front end member.

7. The specimen sorter according to claim 1, wherein the vibration member is moved to collide with the nozzle to form the liquid droplets.

8. The specimen sorter according to claim 1, wherein the nozzle is moved to collide with the vibration member to form the liquid droplets.

9. The specimen sorter according to claim 1, wherein the vibration member includes two side members, and the dispensing nozzle is shook between the side members to collide with the side members alternately one after another.

10. A method of sorting a specimen, comprising:
    removing a specimen from a container;
    identifying the specimen as a target specimen or a non-target specimen; and
    dispensing the specimen, the dispensing the specimen comprising:
        forming liquid droplets at a front end of a dispensing nozzle by moving one of the dispensing nozzle and a vibration member relative to the other of the vibration member and the dispensing nozzle from a position in which the vibration member is not in contact with the dispensing nozzle to a position in which the vibration member and the dispensing nozzle collide;
        dispensing the liquid droplets from the dispensing nozzle;
        collecting, in a first container, the liquid droplets dispensed from the dispensing nozzle that contain the target specimen; and
        collecting, in a second container, the liquid droplets dispensed from the dispensing nozzle that contain the non-target specimen.

11. The method according to claim 10, wherein the dispensing further comprises:
    moving the first container and the second container to collect the liquid droplets.

12. The method according to claim 10, wherein the dispensing further comprises:
    collecting, in a third container, the liquid droplets dispensed from the dispensing nozzle that contain the target specimen; and
    collecting, in a fourth container, the liquid droplets dispensed from the dispensing nozzle that contain the non-target specimen.

13. The method according to claim 12, wherein the dispensing further comprises:
    moving the first container, the second container, the third container, and the fourth container to collect the liquid droplets.

14. The method according to claim 10, wherein the forming the liquid droplets in the dispensing nozzle includes generating a predetermined vibration to form the liquid droplets when the dispensing nozzle and the vibration member collide.

15. The method according to claim 10, wherein the forming liquid droplets includes moving a vibration member to collide with a front end member at the front end of the nozzle.

16. The method according to claim 10, wherein the forming the liquid droplet includes moving the vibration member to collide with the nozzle to form the liquid droplets.

17. The method according to claim 10, wherein the forming the liquid droplet includes moving the nozzle to collide with the vibration member to form the liquid droplets.

18. The method according to claim 10, wherein the forming liquid droplets further comprises:
    shaking the dispensing nozzle between two side members of the vibration member so that the dispensing nozzle collides with the side members alternately one after another.

* * * * *